(12) United States Patent
Hiserodt

(10) Patent No.: US 7,175,839 B1
(45) Date of Patent: Feb. 13, 2007

(54) CANCER IMMUNOTHERAPY USING ALLOSTIMULATED CELLS IN A MULTIPLE SEQUENTIAL IMPLANTATION STRATEGY

(75) Inventor: John C. Hiserodt, Huntington Beach, CA (US)

(73) Assignee: Meyer Pharmaceuticals LLC, Irvine, CA (US)

( * ) Notice: Subject to any disclaimer, the term of this patent is extended or adjusted under 35 U.S.C. 154(b) by 0 days.

(21) Appl. No.: 09/162,648

(22) Filed: Sep. 29, 1998

Related U.S. Application Data

(60) Provisional application No. 60/102,175, filed on Sep. 28, 1998, provisional application No. 60/061,766, filed on Oct. 10, 1997, provisional application No. 60/061,622, filed on Oct. 9, 1997.

(51) Int. Cl.
  A01N 63/00 (2006.01)
  C12N 5/00 (2006.01)
  C12N 5/02 (2006.01)
  C12P 19/28 (2006.01)

(52) U.S. Cl. .................. 424/93.1; 424/93.3; 435/85.1; 435/85.7; 435/325; 435/373; 435/375; 435/810

(58) Field of Classification Search ............ 424/85.1, 424/85.7, 93.1, 93.71, 93.21, 93.2, 93.3; 435/325, 335, 343.1, 344, 372, 343.2, 375, 435/85.1, 85.7, 373, 810
See application file for complete search history.

(56) References Cited

U.S. PATENT DOCUMENTS

| | | | |
|---|---|---|---|
| 5,192,537 A | 3/1993 | Osband | 424/85.2 |
| 5,308,626 A | 5/1994 | Landucci et al. | 424/93.1 |
| 5,484,596 A | 1/1996 | Hanna, Jr. et al. | 424/277.1 |
| 5,602,305 A | 2/1997 | Pober et al. | 800/2 |
| 5,663,481 A | 9/1997 | Gallinger et al. | 800/2 |
| 5,837,233 A * | 11/1998 | Granger | 424/93.1 |
| 5,928,639 A * | 7/1999 | Slavin | 424/93.71 |

FOREIGN PATENT DOCUMENTS

| | | |
|---|---|---|
| EP | 0 379 554 B1 | 5/1996 |
| WO | WO 91/01760 | 2/1991 |
| WO | WO 96/29394 | 9/1996 |
| WO | WO 98/04282 | 2/1998 |
| WO | WO 98/16238 | 4/1998 |
| WO | WO 99/18981 | 4/1999 |
| WO | WO 99/19462 | 4/1999 |

OTHER PUBLICATIONS

Jung et al. Clin Exp Immunology, 81(3): 466-474, Sep. 1990.*
Haugland RP, Handbook of Fluorescent Probes and Research Chemicals. 5th Ed. Molecular Probes, Inc. pg 172-175, 1992.*
Fleshner et al. Cell Transplantation. 1(4): 307-312, 1992.*
Klassen, D.J. et al., "Treatment of Locally Unresectable Cancer of the Stomach and Pancreas: A Randomized Comparison of 5-Fluorouracil Alone with Radiation Plus Concurrent and Maintenance 5-Fluorouracil — An Eastern Cooperative Oncology Group Study" *J. Clin. Oncol.* 3(3):373-378 (1985).
Kruse, C.A. et al., "Intracranial administrations of single or multiple source allogeneic cytotoxic T lymphocytes: Chronic therapy for primary brain tumors" *J. Neuro-Oncol.* 19:161-168 (1994).
Kruse, C.A. et al., "Development of Human Allogeneic CTL in an Artificial Capillary System for Intracavity Treatment of Malignant Glioma" *Proc. Am. Assoc. Cancer Res.* 36:474 Abstract No. 2822 (1995).
Kruse, C.A. et al., "Analysis of interleukin 2 and various effector cell populations in adoptive immunotherapy of 9L rat gliosarcoma: Allogeneic cytotoxic T lymphocytes prevent tumor take" *Proc. Natl. Acad. Sci. USA* 87:9577-9581 (1990).
Kruse, C.A. et al., "Immune Therapy of Recurrent Malignant Gliomas: Intracavity Allogeneic Cytotoxic T Lymphocytes and Human Recombinant Interleukin-2" *FASEB J.10*:A 1413 Abstract No. 2387 (1996).
Mallinson et al., "Chemotherapy in pancreatic cancer: results of a controlled, prospective, randomised, multicentre trial" *Br. Med. J.* 281:1589-1591 (1980).
Merchant, R.E. et al., "Immunotherapy for malignant glioma using human recombinant interleukin-2 and activated autologous lymphocytes" *J. Neuro-Oncol.* 8:173-188 (1990).
Miller, T.R. and Fuller, L.M., "Radiation Therapy of Carcinoma of the Pancreas" *Am. J. Roentgenol.* 80(5):787-792 (1958).
Redd, J.M. et al., "Allogeneic tumor-specific cytotoxic T lymphocytes" *Cancer Immunol. Immunother.* 34:349-354 (1992).
Rosenberg, S.A. et al., "Gene Transfer into Humans: Immunotherapy of Patients with Advanced Melanoma, Using Tumor-Infiltrating Lymphocytes Modified by Retroviral Gene Transduction" *New Engl. J. Med.* 323:570-578 (1990).
Schirrmacher, V. et al., "Workshop: Active specific immunotherapy with tumor cell vaccines" *J. Cancer Res. Clin. Oncol.* 121:487-489 (1995).
Vilmann, P. et al., "Endoscopic ultrasonography-guided fine-needle aspiration biopsy of lesions in the upper gastrointestinal tract" *Gastrointest. Endosc.* 41(3):230-235 (1995).
Wiersema, M.J. et al., "Endosonography-guided real-time fine-needle aspiration biopsy" *Gastrointest. Endosc.* 40(6):700-707 (1994).
Zarling et al., "Generation of cytotoxic T lymphocytes to autologous human leukaemia cells by sensitisation to pooled allogeneic normal cells" *Nature* 274:269-271 (1978).

(Continued)

*Primary Examiner*—Shin-Lin Chen
(74) *Attorney, Agent, or Firm*—J. Michael Schiff

(57) ABSTRACT

This invention provides medicaments and methods for managing cancer using donor cells that are alloactivated in culture. Alloactivated cells are implanted into the bed of a solid tumor and initiate a response by the host against the tumor. Subsequently, alloactivated cells are implanted into the bed of a solid tumor a second time. The two implants work synergistically to confer remarkable benefit to the treated subject, both in terms of management of the cancer and the development of an anti-cancer immune response. The beneficial effects may include regression of the tumor and extended survival. Removal of any residual tumor after the second implant facilitates ongoing resistance to tumor regrowth or metastasis.

13 Claims, 7 Drawing Sheets

OTHER PUBLICATIONS

Bernhard, H. et al., "Treatment of advanced pancreatic cancer with 5-fluorouracil, folinic acid and interferon alpha-2A: results of a phase II trial" *Br. J. Cancer 71*:102-105 (1995).

Chang, K.J. et al., "Endoscopic ultrasound-guided fine-needle aspiration of pancreatic carcinoma" *Am. J. Gastroenterol.* 89(2):263-266 (1994).

Chang, K.J. et al., "Phase I Clinical Trial of Allogeneic Mixed Lymphocyte Culture (Cytoimplant) Delivered by Endoscopic Ultrasound (EUS)-guided Fine Needle Injection (FNI) in Patients with Advanced Pancreatic Carcinoma" *Gastroenterology 112*:A546 (1995).

Chang, K.J. et al., "Endoscopic ultrasound-guided fine-needle aspiration" *Gastrointest. Endosc. 40*(6):694-699 (1994).

Frey, C. et al., "Randomized Study of 5-FU and CCNU in Pancreatic Cancer" *Cancer 47*:27-31 (1981).

Gastrointestinal Tumor Study Group, "Radiation Therapy Combined with Adriamycin or 5-Fluorouracil for the Treatment of Locally Unresectable Pancreatic Carcinoma" *Cancer 56*:2563-2568 (1985).

Declaration by Tetsuya Gatanaga Pursuant to 37 CFR § 1.56 Regarding Clinical Trial Conducted under IND-6288 (5 pages).

Appendix A to Declaration by Tetsuya Gatanaga: Curriculum Vitae (15 pages).

Appendix B to Declaration by Tetsuya Gatanaga: Data from Clinical Trial, Protocol AIT-PAN-20 (12 pages).

Hidalgo et al., J. Clin. Oncol. 17:585-92, 1999. "Phase I-II study of gemcitabine and fluorouracil as a continuous infusion in patients with pancreatic cancer" (Abstract only).

Dugan et al., Pancreas 17:325-33, 1998. "Current concepts in pancreatic cancer: Symposium summary" (Abstract only).

Stephens, Oncol. Nurs. Forum 25:87-93, 1998. "Gemcitabine: A new approach to treating pancreatic cancer" (Abstract only).

Carmichael, Digestion 58:503-7, 1997. "Clinical response benefit in patients with advanced pancreatic cancer. Role of gemcitabine" (Abstract only).

Burris et al., Eur. J. Cancer 33:S18-22, 1997. "Assessing clinical benefit in the tratment of pancreas cancer. Gemcitabine compaed to 5-fluorouracil" (Abstract only).

Rotherberg et al., Ann. Oncol. 7:347-53, 1996. "A phase II trial of gemcitabine in patients with 5-FU-refractory pancreas cancer" (Abstract only).

Carmichael et al., Br. J. Cancer 73:101-5, 1996. "Phase II study of gemcitabine in patients with advanced pancreatic cancer" (Abstract only).

Casper et al., Invest. New Drugs 12:29-34, 1994. "Phase II trial of gemcitabine (2,2'-difluorodeoxycytidine) in patients with adenocarcinoma of the pancreas" (Abstract only).

Burris et al., J. Clin. Oncol. 15:2403-13, 1997. "Improvements in survival and clinical benefit with gemcitabine as first-line therapy for patients with advanced pancreas cancer: A randomized trial" (Abstract only).

Michael et al., Oncology (Huntingt) 11:1615-22, 1625-7, 1997. "Clinical experience with gemcitabine in pancreatic carcinoma" (Abstract only).

\* cited by examiner

CANCER IMMUNOTHERAPY USING ALLOSTIMULATED CELLS IN A MULTIPLE SEQUENTIAL IMPLANTATION STRATEGY

CROSS REFERENCE TO RELATED APPLICATIONS

This application claims priority benefit under 35 USC § 119(e) to U.S. provisional application Nos. 60/061,622 filed Oct. 9, 1997, 60/061,766 filed Oct. 10, 1997, and 60/102,175, filed Sep. 28, 1998. The contents of these applications are incorporated herein by reference in their entirety.

FIELD OF THE INVENTION

The present invention relates generally to the fields of cellular immunology and cancer therapy. More specifically, it relates to the improved treatment of tumors or the generation of an anti-tumor immune response by serial implantation of alloactivated allogeneic cells in or around the tumor site.

BACKGROUND

Cancer continues to be a leading cause of mortality around the globe. Traditional regimens of cancer management have been successful in the management of a selective group of circulating and slow-growing solid cancers. However, many solid tumors are resistant to traditional approaches, and the prognosis in such cases is correspondingly grave.

One example is pancreatic cancer, the fifth leading cause of cancer-related deaths in the United States. It is associated with a high mortality rate, with the median survival for untreated patients estimated at approximately 4 months. Aggressive surgical intervention is an option for only about 10% of patients (those with Stage I disease), and extends median survival to ~14.5 months.

The other 90% have locally advanced or metastatic disease, and are considered unresectable. Traditional therapy has only a modest effect on survival. The median survival of patients with Stage II, Stage III or Stage IV disease averages 4.5 months on a chemotherapy regimen of 5-fluorouracyl (5-FU) compared with 3.5 months without treatment (Frey et al., Cancer (1981) 47:27; Mallinson et al., Br. Med. J. (1980) 281:1590; Miller et al., Am. J. Roentgenol. Radium Ther. Nucl. Med. (1958) 80:787). Radiation therapy alone can reduce pain, but there is no significant improvement of survival (Gastrointestinal Tumor Study Group, Cancer (1985) 56:2563). The combination of chemotherapy with external beam radiation therapy has been employed, but there is no good evidence that such combination therapies are effective (Klaasen et al., J. Clin. Oncol. (1985) 3:373).

More recently, the chemotherapeutic agent, Gemcitabine (GEMZAR™) was shown to improve overall median survival to 5.7 months compared with 4.2 months for 5-FU, and had a better clinical benefit index. However, it is clear that even with these newer agents, palliation of the disease is highly temporary.

Another example is brain cancer. Each year, approximately 15,000 cases of high grade astrocytomas are diagnosed in the United States. The number is growing in both pediatric and adult populations. Standard treatments include cytoreductive surgery followed by radiation therapy or chemotherapy. There is no cure, and virtually all patients ultimately succumb to recurrent or progressive disease. The overall survival for grade IV astrocytomas (glioblastoma multiforme) is poor, with ~50% of patients dying in the first year after diagnosis. Because these tumors are aggressive and highly resistant to standard treatments, new therapies are needed.

An emerging area of cancer treatment is immunotherapy. There are a number of immunological strategies under development. One example is the administration of biomodifiers such as cytokines, either systemically or into the tumor site. One pre-clinical study showed that interferon α-2a can augment the cytotoxicity of 5-FU. However, there was no clinical advantage of this over 5-FU alone (Bernhard et al., (1995) 71:102).

Another example is adoptive immunotherapy, using stimulated autologous cells of various kinds. One version is to stimulate autologous lymphocytes ex vivo with tumor-associated antigen to make them tumor-specific (Zarling et al. (1978) Nature 274:269; U.S. Pat. No. 5,192,537). Autologous lymphocytes and killer cells may also be stimulated non-specifically; for example, by culturing with a combination of IL-2 and IFN-γ (U.S. Pat. No. 5,308,626). Peripheral blood-derived lymphocytes cultured in IL-2 form lymphokine-activated killer (LAK) cells, which are cytolytic towards a wide range of neoplastic cells (Merchant et al. J. Neuro-Oncol. 8:173. A further possibility is the use of tumor-infiltrating lymphocytes (TIL), obtained by collecting lymphocytes infiltrating into tumors, and culturing them with IL-2 (Rosenberg et al. (1990) New Engl. J. Med. 323:570). Unfortunately, TILs can only be prepared in sufficient quantity to be clinically relevant in a limited number of tumor types, and remain experimental.

Another form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

International patent application WO 98/04282 (Hiserodt et al.) describes cancer immunotherapy using autologous tumor cells combined with allogeneic cytokine-secreting cells. The vaccines comprise a source of tumor-associated antigen, particularly tumor cells from the patient to be treated, combined with an allogeneic cytokine-secreting cell line. Exemplary cytokines are IL-4, GM-CSF, IL-2, TNF-α, and M-CSF in the secreted or membrane-bound form. The cytokine-producing cells provide immunostimulation in trans to generate a specific immune response against the tumor antigen. Vaccines can be tailored for each type of cancer or for each subject by mixing tumor antigen with an appropriate number of cytokine-producing cells, or with a cocktail of such cells producing a plurality of cytokines at a favorable ratio.

Yet another proposed strategy for immunotherapy is intratumor administration of immune effector cells—such as cytotoxic T lymphocytes that are specific for tumor cell antigens or alloantigens. The proximity of the effector cells to the target is supposed to promote the ability of the administered cells to react with the tumor, generating a graft versus tumor response.

Kruse et al. (*Proc. Natl. Acad Sci. USA,* 87:9377–9381, 1990) analyzed various effector cell populations in adoptive immunotherapy of the 9 L rat gliosarcoma cell line. Different cell populations were prepared that were designed to have a direct effector function against the cancer cells. Included were syngeneic lymphocytes, nonadherent lymphocyte-activated killer (LAK) cells, adherent LAK cells, syngeneic cytotoxic T lymphocytes (CTL) raised against tumor antigens, and allogeneic CTL raised against alloantigens. The allogeneic cytotoxic T lymphocytes were claimed to prevent tumor take. The CTL were prepared by coculturing thoracic duct lymphocytes from one inbred rat strain with spleen cells from rats syngeneic to the challenged animals, under conditions and for a period designed to enrich for cytotoxic effector cells. Treatment was effected by coinjecting the CTL with the tumor cells into the brains of rats in conjunction with recombinant IL-2, and then readministering the CTL on two subsequent occasions. The regimen was claimed to forestall tumor take by 17 days. The authors state that the tumor is successful in the brain, because the brain is an immunologically privileged site which prevents the administered cells from being eliminated before they perform their function. A corollary of this is that the treatment would not be effective at other sites (such as the pancreas and the breast) that are not immunologically privileged.

In a subsequent study, Kruse et al. (*J. Neuro-Oncol.* 19:161–168, 1994) performed intracranial administrations of single or multiple source allogeneic cytotoxic T lymphocytes. In this study, the 9 L cancer cell line was injected into rats only 6 days before the initiation of treatment. A series of four injections of allogeneic T lymphocytes within the next 17 days was per formed, and had the effect of extending the median life span of the rats by 19 days (about the same interval as the treatment protocol). There is no evidence for any lasting effect, despite the fact that four doses of the effector cells are given. This is consistent with the author's hypothesis that the tumoricidal effect is generated by the CTL themselves, and disappears once the administered cells are eliminated.

Two other publications by the same group demonstrates the natural progression of this CTL implantation technology in a direction towards greater enrichment for cells with a direct effector action against the tumor.

J. M. Redd, et al. *Cancer Immunol. Immunother.,* 34:349, 1992 describe a method of generating allogeneic tumor-specific cytotoxic T lymphocytes. CTL were generated in culture from an inbred rat strain allogeneic to the tumor cell line, and selected and enriched as being specific for a determinant expressed only by the tumor. The ultimate goal of the study is to develop CTL lacking specificity for normal brain antigens. Thus, amongst the CTL populations described earlier in Kruse et al. (*Proc. Natl. Acad. Sci.,* supra) tumor specific CTL are preferred over allospecific CTL for use in human therapy.

More recently, Kruse et al. (*Proc. Am. Assoc. Cancer Res.* 36:474, 1995; *FASEB J.* 10:A1413, 1996) briefly outline a clinical study of human brain cancer patients. The patient's lymphocytes were expanded using OKT3 and IL-2, then co-cultured with allogeneic donor cells for 18–21 days in the presence of IL-2. Such culture conditions would result in a population highly enriched for terminally differentiated CTL effector cells. Patients enrolled in the Phase I study received CTL into the tumor bed, and were placed with a catheter for subsequent infusions. Ongoing treatment involved 1 to 5 treatment cycles every other month, with each cycle consisting of 2–3 CTL infusates within a 1 to 2 week period. Again, the ongoing necessity to readminister the cells is consistent with the author's stated objective of providing cells with a direct cytolytic effect on the tumor.

The necessity of ongoing repeated administration of the effector cells to the tumor through a cannula severely curtails the practical utility of this technology, both in terms of expense and the inconvenience to the patient.

In view of the limitations of previously available strategies, new approaches to the treatment of cancer are needed.

Considerable progress was made towards a simpler and more effective immunotherapeutic strategy by the development of alloactivated cell implants. See International Application WO 96/29394, a "Method for Treating Tumors" (G. A. Granger). Stimulated cellular compositions are placed directly into the tumor bed, leading to beneficial effects for patients with different types of cancers. The method can be conducted by coculturing lymphocytes derived from a healthy allogeneic donor with leukocyte stimulator cells obtained from the patient. The alloactivated donor cells are then surgically implanted at the tumor site, resulting in a response against the tumor. Without intending any limitation on the therapeutic composition or method, it is believed that the implanted cells produce a mixture of cytokines which recruit host cells. The recruited host cells then identify both the implanted lymphoid cells and tumor tissue as foreign.

SUMMARY OF THE INVENTION

This invention provides medicaments and methods that can be used in the management of cancer. Cell populations containing lymphocytes and obtained from at least one third-party donor are alloastimulated using leukocytes (either from the patient to be treated or from another third-party donor). Alloactivated cells are placed in or around a tumor site in the patient on at least two successive occasions. The successive administrations have a synergistic effect in promoting a response by the host against the cancer that stabilizes or resolves the disease.

An embodiment of this invention is the use of one or more cell populations containing alloactivated lymphocytes that are allogeneic to leukocytes of a human patient, in the manufacture of a series of medicaments for sequential treatment of the human or animal body by surgery or therapy. The medicaments may be used for the treatment of cancer (or for eliciting an anti-cancer immunological response) in the patient by sequential implantation into one or more tumor sites. Preferably, the second medicament is implanted at a time when the patient has a demonstrable anti-cancer immunological response from implantation of the first medicament. The combined therapy preferably confers resistance to regrowth or metastasis of the tumor following resection or partial resection of any residual tumor following the implanting of the second medicament.

Another embodiment of this invention is the use of a cell population containing alloactivated lymphocytes that are allogeneic to leukocytes of a human patient in the manufacture of a medicament for the treatment of cancer (or for eliciting an anti-cancer immunological response) in the patient by implanting at a tumor site—either at a time before subsequent treatment of the patent by implanting another medicament containing alloactivated lymphocytes at a tumor site, or at a time following previous treatment of the patent by implanting another medicament containing alloactivated lymphocytes at a tumor site.

A further embodiment of the invention is a method for treating cancer in a human patient, comprising implanting at or around the site of a tumor in the patient a first cell population containing alloactivated lymphocytes that are allogeneic to leukocytes in the patient; and implanting at or around the site of a tumor in the patient a second cell population containing alloactivated lymphocytes that are allogeneic to leukocytes in the patient. The steps are generally separated by at least three days, and are preferably far enough apart for the first cell population to stimulate a response in the patient against the tumor before the implanting of the second cell population. Optimally, treatment according to the method causes substantial regression of the tumor in size; lack of recurrence of a tumor after removal; or decrease in rate of formation of metastasis. If the tumor fails to regress on its own, the method may optionally further comprise removal of any residual tumor mass.

Yet another embodiment of this invention is a pharmaceutical composition comprising alloactivated lymphocytes allogeneic to leukocytes in a cancer patent intended for the treatment of the patient according to a method of this invention.

Additional embodiments of the invention will be apparent from the description that follows.

DETAILED DESCRIPTION

Figure 1A:
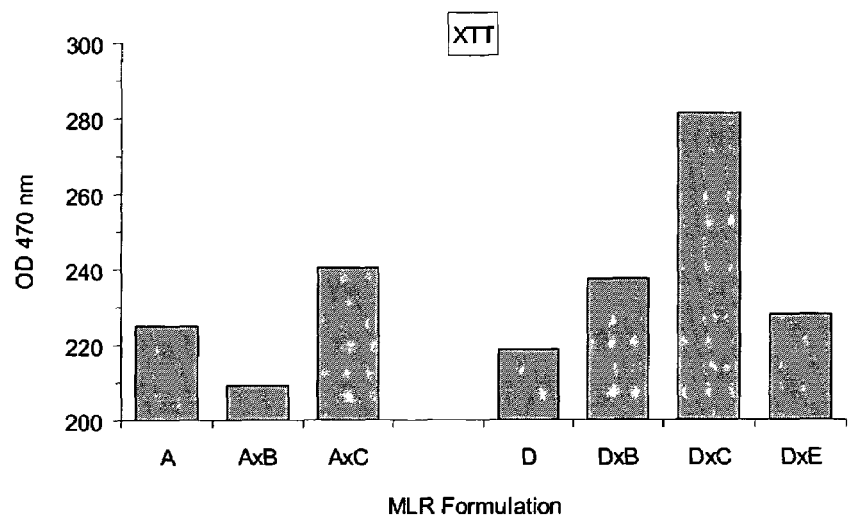
FIG. 1 is a bar graph showing the degree of functional activity in different human alloactivated cell preparations measured in in vitro culture in four different assays.
Figure 1B:
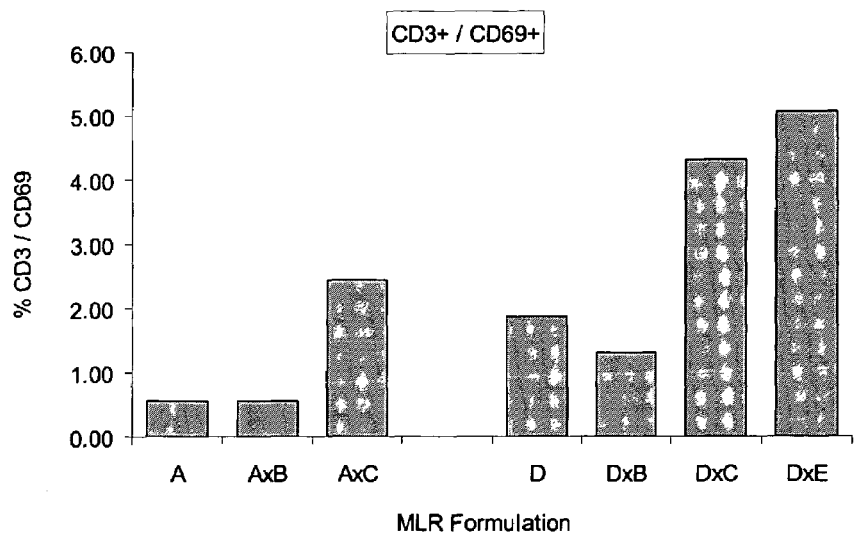
Figure 1C:
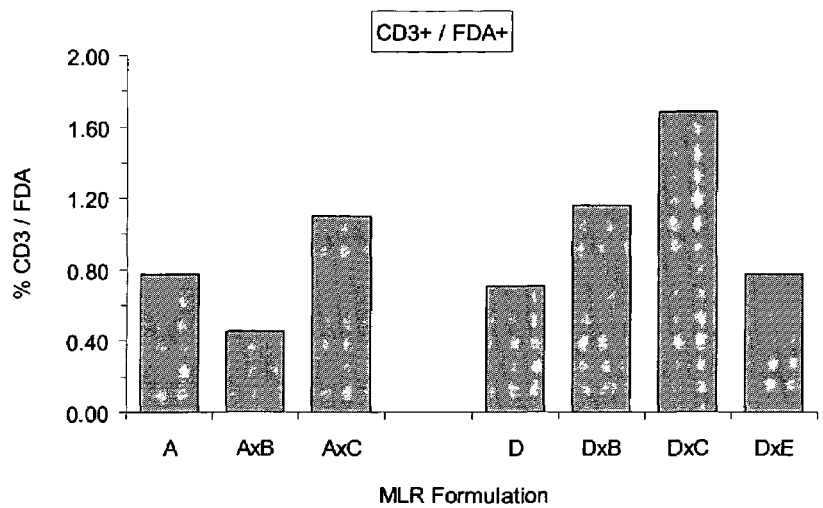
Figure 1D:
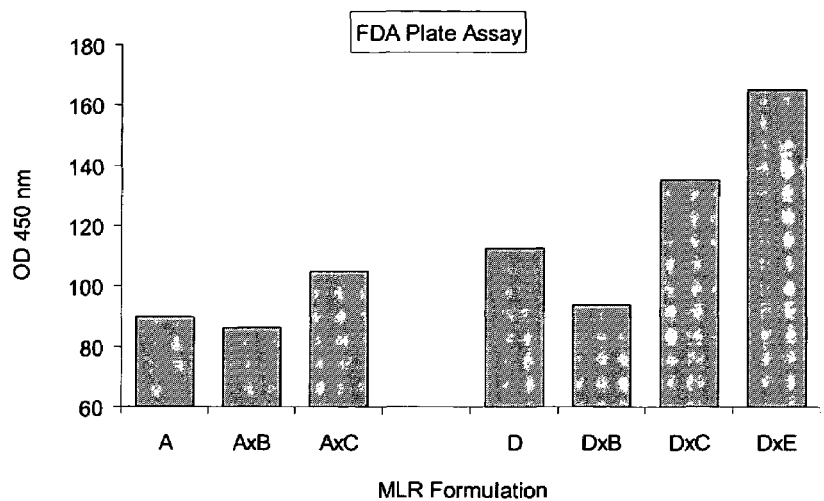

This invention provides a system to manage cancer in an individual, particularly a human patient. The system involves implanting medicaments comprising alloactivated lymphocytes into a tumor site on at least two successive occasions. The successive administrations work synergistically to stimulate a surprisingly potent response by the host against the cancerous cells.

This invention advances the therapeutic potential of the method for treating tumors taught in International Patent Application WO 96/29394. According to the previous disclosure, lymphocytes from a third-party donor are alloactivated by culturing for a brief period with stimulator cells from the patient to be treated. Implantation of alloactivated cells into a tumor site results in a therapeutically beneficial response against the tumor.

The treatment method described in WO 96/29394 has been tested in human patients with brain cancer and with pancreatic cancer. For the treatment of human brain cancer, see Example 2 of WO 96/29394. Subsequently, histology samples became available from several treated patients. One sample set was from a pediatric female diagnosed with glioblastoma multiforme treated with $6 \times 10^9$ cytoimplant cells. The original brain tumor at the time of diagnosis featured palisading necrosis, a pleomorphic tumor infiltrate, and endothelial proliferation, with minimal evidence of inflammation. A biopsy sample taken 30 days after implanting alloactivated cells (stained using H&E or anti-CD45) showed diffuse interstitial infiltrate containing lymphocytes, plasma cells and histiocytes. Another sample was taken from a 56 year old male with anaplastic astrocytoma/gliosarcoma 2 months after treatment. Staining using H&E or anti-CD68 showed infiltrating inflammatory cells, including histiocytes and lymphocytes. Another sample was taken from a 49 year old female with glioblastoma multiforme 6.5 months after treatment. H&E and anti-CD68 staining showed infiltrating lymphocytes and histiocytes.

For the treatment of human pancreatic cancer, see Example 2 below. The median survival for ten patients treated in this study was 11.5 months with a mean survival of greater than 10 months, with doses of at least $9 \times 10^9$ cell proving particularly effective. The survival time for the treated patients was much improved in relation to previously reported times for treatment with 5-fluorouracyl (median 4.2 months) or GEMZAR™ (median 5.7 months). Histology slides were obtained from a patient who died 11.5 months after treatment from unrelated causes. One photomicrograph showed fibrovascular tissue with scattered individualized tumor cells and a dense lymphocytic and plasma cell infiltrate. Another field showed lymphocytes rosetting the separated tumor cells, which showed evidence of apoptosis. In a high magnification view there was clear evidence of direct contact between lymphocytes and necrotic tumor cells.

In these experiements, the single dose of implanted allo-stimulated cells generate a reaction that bears the hallmarks of a mature response. It is particularly significant that the features persist so long after the implantation of the cells. Brain cancer patients showed decreased rates of tumor growth for at least 5 months following treatment, accompanied by ongoing lymphocyte and histiocyte recruitment to the tumor bed. The improved survival in pancreatic cancer extended a median of 11 months after treatment, again with evidence of ongoing lymphocyte recruitment. It is improbable that any material from the implanted cells would remain at the treatment site so long after administration. Even though the implanted cells play a pivotal role in initiating the response, they are not necessary for the response to continue. Without intending any limitation upon practice of this technique, it is hypothesized that the host response resolves its focus onto the tumor itself, presumably at tumor specific antigens not expressed by other tissue. As long as the tumor cells are still present, the tumor specific antigens are available to restimulate the response and recruit cells on an ongoing basis, allowing the response to persist. A single administration of the alloactivated cells is apparently sufficient for the generation of this long-lived and ongoing response.

It has now been discovered that alloactivated lymphocytes implanted into a tumor bed in the patient on at least two sequential occasions have an even more beneficial effect.

It was not predictable that sequential implants would constitute such a substantial improvement. Once a particular treatment regimen fails in a cancer patient, it is usually a sign that the tumor cells have dedifferentiated or evolved to find a way around the metabolic assault of the treatment. The usual course is to switch to a different treatment mechanism, if available, or support the patient for the remaining time by palliative care. As already described, alloactivated cell implants confer an ongoing response, and one would be inclined to interpret failure after a long interval of success as requiring a therapeutic shift. On the other hand, as long as the first cell implant was controlling tumor growth or promoting survival, there would be little reason a priori to undertake the complex procedures necessary for a second implant.

Figure 3:
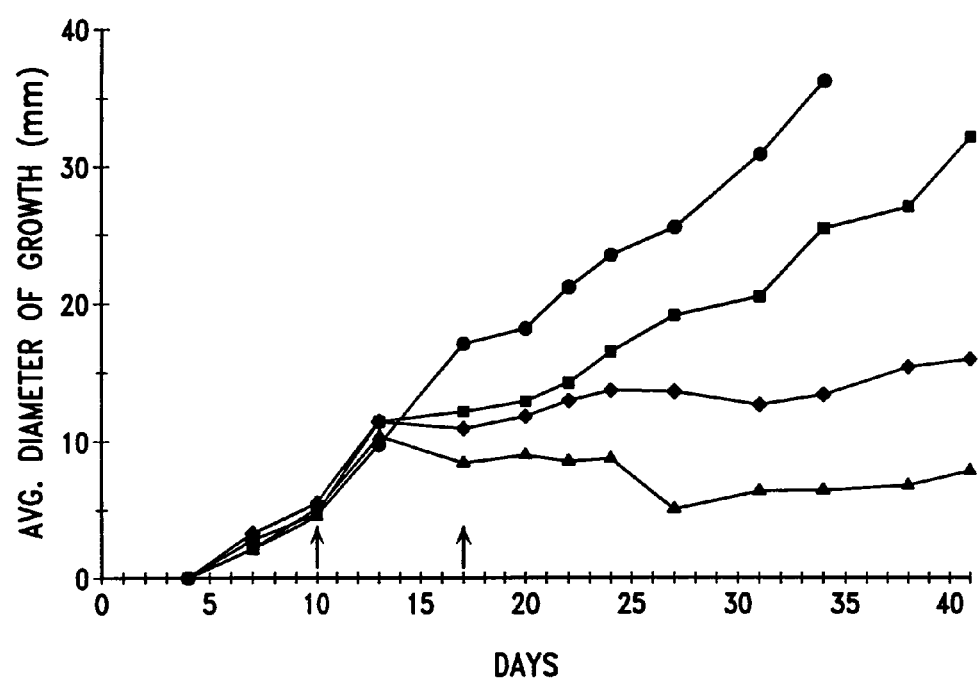
FIG. 3 is a line graph showing the effect of treating the highly lethal D74 tumor cell line in experimental animals (Fischer 344 rats). Group 1: PBS control (●); Group 2: single implant of alloactivated cells at day 10 (Wistar anti-F344) (■); Group 3: two implants of alloactivated cells from the same donor strain on days 10 and 17 (Wistar anti-F344) (▲); Group 4: two implants of alloactivated cells from different donor strains on days 10 and 17 (Wistar anti-F344; Sprague-Dawley anti-F344) (♦). Groups 3 and 4 show significant reduction in the rate of tumor growth. The rate of growth is considerably lower than the animals receiving a single implant (Group 2).

It has been discovered not only that a second implant is beneficial, but that the combined effect of two implants is more than just additive. The second implant doesn't just control tumor growth or extend survival for a similar period as the first. The combined effect of the two implants may convey one or more of the following effects in a substantial proportion of treated subjects:

A significant decrease in size of any unresected tumor—to the point in some subjects where the tumor regresses entirely An extended survival in a significant proportion of treated subjects that is more than twice the extension conferred by a single implant Ongoing immune reactivity against the tumor minimizing regrowth at the original tumor site Ongoing immune reactivity against the tumor minimizing the formation of metastases. Even if the primary tumor does not regress entirely, it can be removed after treatment and the subject will continue to resist tumor progression FIG. 3 illustrates the effect of serial implants on the growth of a tumor line in experimental animals. The tumor growth grows aggressively without treatment (●). A single implant of alloactivated cells (first arrow) delays growth by about 7–10 days, after which growth resumes (■). Two serial implants (first and second arrow) on average stabilizes tumors from further growth (▲, ♦). About half of these animals become long-term survivors, and have complete tumor regression. Animals treated with two implants and then resected of residual tumor are resistant to a subsequent challenge with a lethal dose of tumor cells from the same cell line. The resistance conferred is tumor-specific, which is consistent with an antigen-specific host anti-tumor immunological response.

A further description of preferred embodiments for this invention is provided in the sections that follow.

Definitions

"Mixed lymphocyte reaction" "mixed lymphocyte culture", "MLR", and "MLC" are used interchangeably to refer to a mixture comprising a minimum of two different cell populations that are allotypically different. At least one of the allotypically different cells is a lymphocyte. The cells are cultured together for a time and under suitable conditions to result in the stimulation of the lymphocytes. A frequent objective of an MLC is to provide allogeneic stimulation such as may initiate proliferation of the lymphocytes; but unless indicated, proliferation during the culture is not required. In the proper context, these terms may alternatively refer to a mixture of cells derived from such a culture.

An "implant" or "cytoimplant" in the appropriate context refers to a bolus of alloactivated cells (such as may be derived from an MLC) suitable for administration into a tumor bed in a subject. This is typically performed for eliciting a response in the subject against the tumor or treatment of the tumor.

A "cell line" or "cell culture" denotes higher eukaryotic cells grown or maintained in vitro. It is understood that the descendants of a cell may not be completely identical (either morphologically, genotypically, or phenotypically) to the parent cell.

"Inactivation" of a cell is used herein to indicate that the cell has been rendered incapable of cell division to form progeny. The cell may nonetheless be capable of response to stimulus, or biosynthesis and/or secretion of cell products such as cytokines. Methods of inactivation are known in the art. Preferred methods of inactivation are treatment with toxins such as mitomycin C, or irradiation. Cells that have been fixed or permeabilized and are incapable of division are also examples of inactivated cells.

The term "cancer cell", used either in the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

The term "tumor-associated antigen" or "TAA" refers to a molecule, complex, or epitope that is detected at a higher frequency or density by tumor cells than by non-tumor cells of the same tissue type. Knowledge of the existence or characteristics of a particular tumor-associated antigen target is not necessary for the practice of the invention.

The terms "vaccine", "immunogen", or "immunogenic composition" are used herein to refer to a composition capable of generating or boosting an immune response in an individual, comprising either antibody or immunoreactive cells (such as helper/inducer or cytotoxic cells), or both, and is preferably directed towards an antigen that is present on a tumor towards which the treatment is directed.

As used herein, "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, diminishment of any direct or indirect pathological consequences of the disease, preventing metastasis, lowering the rate of disease progression, amelioration or palliation of the disease state, and remission or improved prognosis.

The "pathology" associated with a disease condition is anything that compromises the well-being, normal physiology, or quality of life of the affected individual. This may involve (but is not limited to) destructive invasion of affected tissues into previously unaffected areas, growth at the expense of normal tissue function, irregular or suppressed biological activity, aggravation or suppression of an inflammatory or immunological response, increased susceptibility to other pathogenic organisms or agents, and undesirable clinical symptoms such as pain, fever, nausea, fatigue, mood alterations, and such other features as may be determined by an attending physician.

An "effective amount" is an amount sufficient to effect a beneficial or desired clinical result, particularly the generation of an immune response, or noticeable improvement in clinical condition. An immunogenic amount is an amount sufficient in the subject group being treated (either diseased or not) sufficient to elicit an immunological response, which may comprise either a humoral response, a cellular response, or both. In terms of clinical response for subjects bearing a neoplastic disease, an effective amount is amount sufficient to palliate, ameliorate, stabilize, reverse or slow progression of the disease, or otherwise reduce pathological consequences of the disease. An effective amount may be given in single or divided doses. Preferred quantities and cell ratios for use in an effective amount are given elsewhere in this disclosure.

A "response" by a host against a tumor it is bearing can be any form of biological reaction mediated by host cells that limits growth of the tumor, increases survival, or meets the other criteria of treatment. Treatment according to this invention typically results in an inflammatory response (evidenced by recruitment of inflammatory mediator cells such as macrophages to the tumor site with inflammatory sequalae) and/or an immune response (evidenced locally by recruitment of lymphocytes to the tumor site; evidenced systemically by the detection of specific humoral or cellular immunity against the tumor cells).

An "individual" or "subject" is a vertebrate, preferably a mammal, more preferably a human. Non-human mammals include, but are not limited to, farm animals, sport animals, and pets.

General Techniques

The practice of the present invention will employ, unless otherwise indicated, conventional techniques of molecular biology, microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991). See also Gately et al., Lee et al., and Zarling et al. (infra) for examples of techniques in mixed lymphocyte cultures.

General procedures for the preparation and administration of pharmaceutical compositions are outlined in *Remington's Pharmaceutical Sciences* 18*th Edition* (1990), E. W. Martin ed., Mack Publishing Co., PA.

There are a number of animal models for cancer that can be used to test and adjust the compositions and methods of this invention, if desired. Certain models involve injecting in-bred animals with established syngeneic tumor lines. The tumors can be co-injected with a potentially therapeutic composition, allowed to establish before therapy is commenced, or administered as a challenge at some time following vaccination of a naive animal. Illustrations are provided in the Example section. Also useful are chimeric animal models, described in U.S. Pat. Nos. 5,663,481, 5,602,305 and 5,476,993; EP application 379,554; and International application WO 91/01760.

All patents, patent applications, articles and publications mentioned herein, both supra and infra, are hereby incorporated herein by reference.

Preparation of Alloactivated Cell Populations

While any suitable method of alloactivation can be used, the cellular compositions of this invention are usually prepared by alloactivating one or more responder cell populations containing lymphocytes with one or more stimulator cell populations expressing alloantigens. The source of the responder and stimulator cells are allogeneic both to each other, and to the patient to be treated with the resultant composition.

Source of cells: According to the usual method of preparing the alloactivated cells, at least two cell populations are required from allogeneic individuals: one to act as responder cells, the other to act as stimulator cells.

Cells are generally described as allogeneic if they are from the same species but bear a phenotypic difference sufficient to stimulate an alloreaction. In the context of this disclosure, use of the term "allogeneic" is restricted to a difference in phenotype of major histocompatibility complex (MHC) antigens. Any qualitative difference in the identity of MHC allotypes between cells of the same species means they are allogeneic cells. In humans, differences at any of the HLA-A, B, C, DP, DQ, and DR loci constitute allotypic differences relevant for this invention., typically determined using allotype-specific antibodies in a cytotoxicity or immunofluorescence technique. Class II phenotype can be determined at the D locus by mixed lymphocyte reaction using typed cells.

Preferred allotypic differences for the purposes of the present invention relate to HLA class II antigens. Comparing the class II antigens of the DP, DQ, and DR loci between the putative allogeneic cells and cells of the subject to be treated, at least one and up to six are different between allogeneic cells. Donors of allogeneic cells are generally unrelated to the subject being treated, to maximize the number of MHC mismatches. In a normal outbred population, unrelated individuals will almost invariably differ at a number of different loci.

The number of class II region mismatches is related but secondary to a functional determination of allogenicity. Allogeneic cells are particularly suitable for use in the present invention if they demonstrate a strong proliferative response when tested in alloreactive cultures. Donors of cells previously known or empirically shown to produce a particularly strong response are especially suitable for use in therapy. As described elsewhere in this disclosure, a panel of different allogeneic cells can be tested in combinations to determine those that elicit the strongest degree of alloactivation.

The "responder" cells are capable of specifically reacting to an allogeneic stimulus.

The contributor of the responder cells is most often a single third-party donor who is allogeneic to the patient, typically a healthy volunteer. To improve alloactivation, unrelated donors are preferred over family members of the patient. Mixtures of two or more third-party donor cells are also contemplated to facilitate collection, to increase stimulation, to minimize the elicitation of an anti-allotype response in the patient, or to otherwise enhance the therapeutic efficacy.

The cell population generally contains lymphocyte cells or cells of the lymphocyte lineage, particularly T cells. Lymphocytes expressing CD4 antigen (CD4+ cells), and cells expressing CD8 antigen (CD8+ cells) are both included in the definition of T lymphocytes, and either or both may be included in the composition. Generally, the responder cells are leukocytes obtained from peripheral blood, typically enriched for mononuclear cells (PBMC), and optionally further enriched for cells of the lymphocyte lineage. Particular enriched populations contain at least 10% CD4+ cells or 10% helper/inducer cells; more preferably they are at least about 20% of CD4+ or helper/inducer cells; even more preferably the portion is at least about 30% of CD4+ or helper/inducer cells. CD4+ cells may be conveniently quantified with commercially available specific antibody such as OKT4 in conjunction with fluorescence-activated counting. However, standard peripheral blood mononuclear cell preparations are suitably enriched for many applications of this invention. Assays for determining the extent of alloactivation are described in the next section.

The "stimulator" cells are allogeneic to the responder cells and capable of eliciting an alloreaction in the responders. Two options are available for the contributor of the stimulator cells. The first is to use cells from the patient who will ultimately be implanted after the cells are cultured. The second is to use another third-party donor who is allogeneic to the donor contributing the responder cells. The donor of the stimulator cells may be unrelated to the patient, or a family member (in which case some allotypes will be shared with the patient). Mixtures of two or more third-party donor cells, or donor cells plus patient cells, can also be used to facilitate collection, to increase stimulation, or to otherwise enhance the therapeutic efficacy.

Suitable cell types for use as stimulator cells are those that bear a high density of allogeneic histocompatibility antigens, particularly class II antigens. Any type of cell (not limited to blood cells) bearing sufficient alloantigens can be used. A particularly suitable source is peripheral blood leukocytes or white cells. It is desirable to enrich for, or at least not to deplete cells expressing class II histocompatibility antigens from the population, such as B cells and monocytes. Extensive subfractionation of the cells is not usually required, and a simple peripheral blood mononuclear cell population (PBMC) is adequate for most purposes.

Collection and preparation of cells: Third-party donors are typically prescreened to identify those with sufficient leukocyte count, and exclude those with neoplastic conditions or transmissible infections. Collection of donor or patient cells can be performed by whole blood donation followed by separation of blood cell populations, or by leukapheresis. Leukapheresis is especially appropriate for collecting the responder cell population, because the number of cells required is substantial. Sufficient blood is processed to obtain about 100–500 mL leukapheresis suspension, preferably at least about 200 mL. For example, leukapheresis may be performed using a Cobe 2997 (COBE SPECTRA®, Lakewood Colo.); Fenwall CS 300 (Fenwall, Deerfield Ill.); or Haemonetrics (Braintree Mass.) blood cell separator. Flow rates of ~40–50 mL/mm for 2–4 h yield ~200–250 mL leukapheresis suspension having <1 mL red cells, with variations between individual donors and the equipment used.

The collected leukocytes are generally washed to remove platelets, and resuspended in a suitable medium, such as AIM V supplemented with 2% inactivated fetal calf serum. Separation of PBMC and other enrichment procedures include centrifugation over a suitable medium such as FICOLL™ or HISTOPAQUE®, passage over a nylon-wool column, affinity separation methods such as panning, or sorting in a fluorescent cell sorter using an antibody against a relevant cell-surface marker. Where possible, it is generally preferable to decrease the number of manipulation steps. For example, better leukapheresis separation may obviate the need for subsequent separation on FICOLL™.

Mixed lymphocyte cultures: Responder and stimulator cells are combined in a suitable culture medium, typically supplemented with fetal calf serum or a serum substitute, and optionally including other growth factors. The ratio of responder:stimulator cells is preferably between about 100:1 to 1:10; more preferably about 50:1 to 1:1; still more preferably about 20:1 to 5:1, and even more preferably about 10:1. Where there are a plurality of stimulator or responder cells in a one-way MLC, the same approximate ratio of responders:stimulators is maintained. Thus, when using 2 inactivated stimulators, the ratio may be approximately 9:(1:1); when using 3 inactivated stimulators, the ratio may be approximately 8:(1:1:1). Similarly, when using multiple responders, the ratio can be (5:5): 1 or (3:3:3): 1. If cultured together, the multiple responder composition becomes a multi-way MLC. One-way activation of multiple responders can be achieved by conducting a separate culture for each responder population at a 10:1 ratio, and then combining the alloactivated cells just before use.

This invention encompasses the use of two-way or multi-way mixed lymphocyte cultures, wherein a plurality of cell populations act as both responders and stimulators. In a frequently employed embodiment of the invention, one-way MLCs are performed by inactivating the stimulator cells, for example, by treating ~$10^7$ cells/mL with 50 µg/mL mitomycin C or sublethal irradiation, followed by washing.

Once combined in the desired ratio, the cells cultured at an appropriate density in a suitable atmosphere (such as 95% $O_2$, 5% $CO_2$ at about 37° C.). The culture period is preferably at least about 12 h, more preferably between about 24 h and 72 h. Additional stimulation may be obtained by culturing for 3–5 days, although this is generally not preferred (depending on other culture conditions), since cytokine levels are normally higher during the first 48 to 72 h of culture.

The recitation within this disclosure of preferred cell sources, cell ratios, culture conditions, timing, and other features, is intended as an aid to the practitioner and is not meant to limit the scope of the invention, unless explicitly required. No limitation is implied with respect to any of the individual parameters, since various other parameter combinations will generate a cell population with the desired functional effect.

Measuring functional criteria of the alloactivated cell population: Once the culture is initiated but before use in therapy, the functional activity of the culture can be determined using one or more functional assays.

Since cytokine secretion is believed to play an important role in eliciting the response in the treated subject, cytokines can be tested in a standard immunoassay. Particular cytokines of interest are IL-2, IL-4, IL-6, TNF-α, LT, IFN-γ, G-CSF, M-CSF (both membrane and secreted form), and GM-CSF. For example, particular degrees of stimulation is indicated by levels of biological activity of TNF-α or LT at 50–150 U/mL, or 500–3500 pg/mL.

Proxies for functional activity of the alloactivated cells include: I: MTT Formazan Reduction Assay; II: XTT Formazan Reduction Assay; III: Flow Cytometry for CD3/CD69 or CD3/FDA; IV: FDA Plate Assay; V: Acid Production Assay; VI. Acridine Orange Assay. These assays are detailed in Example 3. More traditionally, alloactivation can be determined by cell proliferation, measured by culturing a test sample for 5 days and conducting a standard [$^3$H]-thymidine uptake assay, or by counting blast cells. The predictive value of functional assays can be determined by comparing results of the assays on cultured cells with the effect of the cells in a suitable animal model.

Preferred cultures are those that show a level of activation ≧10% above unstimulated donor control value within one of the first 3 days of culture, as measured by a suitable assay such as the Acridine Orange Assay (AO), or by Flow Cytometry (CD69), or both. Where cultures do not meet these criteria, a new donor for the responder or stimulator cell population can be selected and the culture can be repeated in an attempt to obtain better functional activity. Most combinations of human cells between unrelated responder and stimulator populations achieve the minimum activation level under proper culture conditions, and functional testing of the cultured cells is not absolutely required for the practice of the invention.

Cells intended for human administration are also typically tested for sufficient sterility, and to ensure that a minimum number of cells are present and viable.

Optimizing the functional effect: Several optional steps can be taken to increase the degree of alloactivation in the lymphocyte culture.

Not all donors provide the same degree of alloactivation, either as responder or stimulator cells. Lymphocytes from a plurality of potential donors can be tested using the functional assays described earlier, or according to the level of secretion of certain lymphokines determined by ELISA. Once successful donors are identified, they can be constituted in a panel of regular donors sourced by the service lab providing the immunogenic compositions. Efficacy of certain donor-patient combinations may also migrate according to histocompatibility, and donors can be selected, if desired, on the basis of tissue match.

Since the response is thought to involve cytokine secretion by the alloactivated cells, an alternative predictor of strong responder-stimulator combinations may be a two-stage culture. In this approach, a responder:stimulator culture is set up using the same responder and stimulator cells being tested for use in the preparative culture. At 3 days, the culture is inactivated with mitomycin or sub-lethal irradiation, so that cells can still produce cytokines but not replicate. Leukocytes from the patient are then added, and their response is followed by a functional assay, cytokine secretion, or T cell proliferation. In a variation of this approach, inactivated tumor cells are also provided in the second stage of the culture, and read-out is determined at the end of the second stage by measuring cytolysis of $^{51}$Cr labeled tumor cells.

As an alternative or in addition to pretesting the responder:stimulator:recipient combination, the degree of alloactivation or the potential therapeutic outcome can be enhanced by employing either of the following strategies: a) using a plurality of donor cells as the responder or stimulator in the MLC; and/or b) adding an 112 receptor antagonist to the culture medium of the MLC.

Using a plurality of donors for the responder or stimulator cell population confers a number of advantages. It is predicted that there will be a normalizing effect—when there is a variety of alloincompatibilities present, there is a stronger possibility that at least one stimulator cell will stimulate at least one responder cell, and in turn, that at least one responder cell will stimulate the treated subject. It is also more convenient, in that the same mixed population will be suitable for a variety of patients. Thus, a large batch of mixed alloactivated cells can be prepared and stored frozen, for dispensation on demand. It has also been discovered that having a plurality of different stimulators can achieve levels of alloactivation higher than one of the stimulators alone.

Adding an H2 receptor antagonist to the culture medium also has an enhancing effect on alloactivation during the first three days of culture. Without intending to be bound by theory, it is hypothesized that the H2 receptor antagonist inhibits the activity of suppressor T cells in the culture. Thus, including an H2 receptor antagonist can be an effective adjunct during culture of cell combinations that are known to be allogeneic, but show little reactivity in a standard MLC. A preferred H2 receptor antagonist is cimetidine, added to the culture medium at between 5 μg/mL and 100 μg/mL, typically 20 μg/mL.

These techniques are described for the benefit of the reader who may wish to optimize the compositions of this invention in various ways, or to set up a donor panel enriched for high responders, or for treatment of an unusually resistant patient. The invention can be practiced in full without employing any of these optional procedures, as illustrated in the example section below.

Use of Cellular Compositions in Cancer Treatment

Medicaments comprising alloactivated cells prepared according to this disclosure can be administered to subjects, especially human subjects. They are particularly useful for eliciting an immune response against a tumor-associated antigen, or for treating cancer.

Objectives of treatment: One purpose of implanting the medicaments of this invention is to elicit a tumor-specific immune response. The immune response may include either humoral or cellular components, or both. Humoral immunity can be determined systemically by a standard immunoassay for antibody levels in a serum sample from the treated individual.

Since cellular immunity is thought to play an important role in immune surveillance of cancer, generating a cellular immune response is frequently a particular objective of treatment. As used herein, a "cellular immune response" is a response that involves T cells, and can be observed in vitro or in vivo.

A general cellular immune response can be measured as the T cell proliferative activity in cells (particularly PBL) sampled from the subject after administration. Inactivated tumor cells, preferably derived from the subject, are used as stimulators A non-specific mitogen such as PHA serves as a positive control; incubation with an unrelated stimulator cell serves as a negative control. After incubation of the PBMCs with the stimulators for an appropriate period (typically 5 days), [$^3$H]thymidine incorporation is measured. If desired, determination of which subset of T cells is proliferating can be performed using flow cytometry. T cell cytotoxicity (CTL) can also be measured. In this test, an enriched T cell population from the subject are used as effectors in a standard $^{51}$Cr release assay. Tumor cells are radiolabeled as targets with about 200 μCi of Na$_2$ $^{51}$CrO$_4$ for 60 minutes at 37° C., followed by washing. T cells and target cells (~$1\times10^4$/well) are then combined at various effector-to-target ratios in 96-well, U-bottom plates. The plates are centrifuged at 100×g for 5 minutes to initiate cell contact, and are incubated for 4–16 hours at 37° C. with 5% $CO_2$. Release of $^{51}Cr$ is determined in the supernatant, and compared with targets incubated in the absence of T cells (negative control) or with 0.1% TRITON™ X-100 (positive control). Specificity of the immune response in any of these assays can be confirmed by comparing the results with reactivity observed against an unrelated cancer cell line.

Evidence of a host response can be shown inter alia by infiltration of host leukocytes (such as lymphocytes, histiocytes, and other leukocytes) into the tumor site by standard histomorphology analysis. Evidence of a local immune response near the tumor site can be obtained in histopathology samples taken during surgery, biopsy, or autopsy. Infiltration of lymphocytes to the site beyond the number accountable from the implant itself is evidence of immune recruitment. The infiltrating cells can be further characterized for cell-surface markers.

Another purpose of implanting the cellular compositions of this invention is for treatment of a neoplastic disease, particularly cancer. Beneficial effects are typically immunologically mediated or the result of an inflammatory infiltrate into the injection site and collateral tumors. However, the mechanism of obtaining the beneficial effect need not be elucidated if significant clinical improvement is obtained.

Possible criteria for gauging clinical benefit include those outlined in Example 8. Desirable outcomes include the following:

Significant decrease in the rate of tumor growth—preferably to less than 50% of the growth of untreated tumors; more preferably a stabilization of tumor size; even more preferably a partial or complete regression. Tumor size can be measured by calipers, upon resection or by imaging techniques such as CT scan ultrasound, MRI, or radioscintigraphy.

Extended survival—preferably by a median of at least 5 months, more preferably by a median of at least 10 months or by more than double the untreated expectancy, depending on the type and staging of the tumor Decreased risk of recurrence of a resected tumor—preferably to less than half of the untreated risk Decreased rate of metastasis formation—preferably to less than half of the untreated rate Evidence of attaining these criteria can come by tracking disease progression in a particular individual before and after treatment. It can also come by comparing the outcome of a group of treated patients with concurrent or previous experience with patients treated by other approaches. Preferably, at least 30% of the treated group will show evidence of efficacy according to at least one of the criteria listed above. More preferably, 50% or even 70% will show clinical efficacy.

Medicaments comprising alloactivated cells according to this description fall within the scope of the invention if they are intended for use in cancer subjects with an expectation of clinical outcome meeting these criteria, regardless of whether they are actually administered to a patient. Methods of treatment according to this description fall within the scope of the invention if they are performed on a cancer subject with an expectation of clinical outcome meeting these criteria, regardless of whether the particular patient derives the desired benefit.

Suitable subjects: The compositions of this invention may be used for administration to both human and non-human vertebrates.

Typically, the subject will either have cancer, or be at considerable risk of developing cancer. Typical human subjects for therapy comprise two groups, which may be distinguished by clinical criteria. Patients with "advanced disease" or "high tumor burden" are those who bear a clinically measurable tumor that can be detected on the basis of tumor mass (e.g., by palpation, MRI, CAT scan, X-ray, or radioscintigraphy; positive biochemical or histopathological markers on their own are insufficient to identify this population).

A cellular composition for use in this invention is administered to patients with advanced disease with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known as the "adjuvant group". These are individuals who have had a history of cancer, but have been responsive to another mode of therapy. The prior therapy can have included (but is not restricted to) surgical resection, radiotherapy, traditional chemotherapy, and other modes of immunotherapy. As a result, these individuals have no clinically measurable tumor by the definition given above. However, they are suspected of being at risk for recurrence or progression of the disease, either near the original tumor site, or by metastases. The adjuvant group may be further subdivided into high-risk and low-risk individuals. The subdivision is made on the basis of features observed before or after the initial treatment. These features are known in the clinical arts, and are suitably defined for each different cancer. Features typical of high risk subgroups are those in which the tumor has invaded neighboring tissues, or which show involvement of lymph nodes.

A cellular composition for use in this invention is administered to patients in the adjuvant group in order to elicit an anti-cancer response primarily as a prophylactic measure against recurrence. Ideally, the composition delays recurrence of the cancer, or more preferably, reduces the risk of recurrence (i.e., improves the cure rate). Such parameters may be determined in comparison with other patient populations and other modes of therapy.

Of course, crossovers between these two patient groups occur, and the cellular compositions can be administered at any time that is appropriate. For example, therapy can be conducted before or during traditional therapy of a patient with high tumor burden, and continued after the tumor becomes clinically undetectable. Therapy may be continued in a patient who initially fell in the adjuvant group, but is showing signs of recurrence.

Examples of tumors that can be treated according to this invention include but are not limited to those on the following list. The list includes sites that are thought to be immune privileged, such as the brain, and sites that are not immune privileged, such as the pancreas, colon, breast, and prostate.

Brain tumors, such as astrocytoma, oligodendroglioma, ependymoma, medulloblastomas, and PNET (Primitive Neural Ectodermal Tumor);

Pancreatic tumors, such as pancreatic ductal adenocarcinomas.

Lung tumors, such as small and large cell adenocarcinomas, squamous cell carcinoma, and bronchoalveolar-carcinoma;

Colon tumors, such as epithelial adenocarcinoma, and liver metastases of these tumors;

Liver tumors, such as hepatoma, and cholangiocarcinoma;

Breast tumors, such as ductal and lobular adenocarcinoma;

Gynecologic tumors, such as squamous and adenocarcinoma of the uterine cervix, and uterine and ovarian epithelial adenocarcinoma;

Prostate tumors, such as prostatic adenocarcinoma;

Bladder tumors, such as transitional, squamous cell carcinoma;

Tumors of the RES System, such as B and T cell lymphoma (nodular and diffuse), plasmacytoma and acute and chronic leukemia;

Skin tumors, such as malignant melanoma; and

Soft tissue tumors, such as soft tissue sarcoma and leiomyosarcoma.

Generally, the individual will be immunologically naive with respect to tumor-associated antigens present in the composition. The individual may have anti-tumor immunity, apparent or present as immunological memory, resulting from previous exposure to tumor-associated antigen, for example, in a previously administered vaccine composition. In any case, the subject should be at least partly immunocompetent, so as to minimize excessive graft versus host reaction, and so as to be able to mount a host response to the implant. It is recognized that cancer patients often show a degree of immunosuppression, and this does not necessarily prevent the use of the compositions according to the invention, as long as the compositions may be given safely and effectively.

Modes of administration and dose: The compositions of this invention can be administered to the subject at the site of any solid tumor. Circulating cancers are treatable so long as there is at least one solid tumor mass. Metastatic sites, affected nodes, and other sites away from the primary neoplasm are suitable, so long as they are accessible and contain sufficient tumor antigen.

If the solid tumor mass is resectable or partly resectable, then the composition can be administered at or near the site or in a cavity created by the resection. The most convenient time to administer the alloactivated cells to a resectable site is during the time of surgery. To keep the cells at the site until completion of the surgical procedure, it is convenient to administer the cells in a pharmaceutically compatible artificial gel, or in clotted plasma. Efficacy of the implant is probably enhanced by the presence of a certain number of tumor cells to provide bystander antigen. Residual tumor cells at the primary site may be sufficient. However, if the tumor is completely removed, it may be preferable to administer the alloactivated cells not to the primary site but to a metastasis, so that sufficient tumor antigen will be nearby.

When the solid tumor mass is not resectable, or where less invasive procedures are desired, then the composition can be injected at or near the tumor site through a needle. For deeper sites, the needle can be positioned using ultrasound, radioscintigraphy, or some other imaging technique, alone or in combination with the use of an appropriate scope or cannula. Pancreatic tumors are preferably implanted using an injection needle positioned by an endoscopic ultrasound guided technique, as described by Chang et al., *Gastroenterology* 112:A346, 1996. See Example 7, below. For this application, the cell population is conveniently administered when suspended in isotonic saline or a neutral buffer to a volume of about 10 mL.

The dose given is an amount "effective" in bringing about a desired therapeutic response, be it the stimulation of an immune response, or the treatment of cancer as defined elsewhere in this disclosure. For the pharmaceutical compositions of this invention, effective doses typically fall within the range of about $10^8$ to $10^{11}$ cells, including allogeneic stimulators and responders. Preferably, between about $1 \times 10^9$ to $5 \times 10^{10}$ cells are used; more preferably between about $2 \times 10^9$ to $2 \times 10^{10}$. Multiple administrations when used in combination to achieve a desired effect each fall within the definition of an effective amount. For example, it is acceptable to divide a dose for simultaneous administration to several small tumors in the same individual.

The various components of the cellular vaccine are present in an "effective combination", which means that there are sufficient amounts of each of the components for the vaccine to be effective. Preferably, at least about $10^8$, more preferably between about $1 \times 10^9$ to $5 \times 10^{10}$ and; more preferably between about $2 \times 10^9$ to $2 \times 10^{10}$ responder cells are present. Preferably, at least about $10^7$, more preferably between about $5 \times 10^7$ to $5 \times 10^9$ and; more preferably between about $1 \times 10^8$ to $2 \times 10^9$ stimulator cells are present. Ratios of allogeneic lymphocytes to stimulator leukocytes is generally between 1:1 and 100:1, usually between about 5:1 and about 25:1, and typically about 10:1. However, any number of component cells or other constituents can be used, as long as the composition is effective as a whole. This will also depend culture conditions and other factors during preparation.

Timing of the sequential administrations: The medicaments and treatments of this invention relate to multiple serial administration to the cancer subject on at least two occasions. The first medicament comprising the alloactivated cells is implanted in or around the site of a solid tumor in the subject, with or without prior resection or partial resection. After a suitable interval, the second medicament is implanted.

There are several options for the choice of the time interval. Generally, the interval is at least three days, and is typically longer. In one embodiment of the invention, the interval is between about one and twelve weeks, more typically between one and eight weeks, and even more typically between two and four weeks. In another embodiment of the invention, the interval is between one month and two years, more typically between two and twelve months, and even more typically between four and eight months. Shorter intervals may be employed for aggressive tumors or easily accessible tumors where the synergistic effect is desired at an earlier time. Shorter intervals are also appropriate for non-human subjects. Longer intervals may be employed in other situations, such as when access to the tumor is restricted. Optionally, the subject may be tested for evidence of an immunological anti-tumor response resulting from the first implant before administering the second. A suitable assay is a one-way MLTR, in which patient lymphocytes respond to inactivated tumor cells. However, the immunological response is likely to be in place and there is no requirement to undertake this test, particularly if the interval between administrations is four weeks or more.

The second medicament is tyically composed of about the same number of alloactivated cells as the first, although variations are permitted. The donor of the responder cells may be either the same donor used for the preparation of the first medicament, or a different one. Both combinations work, as shown in Example 5. There is a possibility that the allogeneic lymphocytes in the composition may generate an anti-allotype response. The use of different donors (or a mixture of donors) in each composition may help decrease this possibility. If the stimulator cells of the first medicament were taken from the patient, it is usual that the same stimulators be used for the second medicament, although this is not required.

The second medicament is also implanted in or around the site of a tumor in the subject, with or without resection or partial resection. The tumor site selected is often the same as the one used for the first imiplantation, but may vary depending on circumstances. For example, if the first implant is at the site of the primary tumor, and there is evidence of regrowth in the intervening time, then the second implant may be made during surgical procedure to remove the new growth. However, where the first tumor has regressed but there are a number of satelite or metastatic tumors, it can be more desirable to administer the second medicament to one or more of these secondary sites.

This invention also contemplates multiple serial implantation of three or more than three medicaments, for purposes of further accentuating the beneficial effects. The time interval between the second implant and subsequent implants is generally about the same or longer as between the first and the second, although it may be desirable to accelerate the schedule upon evidence of a deteriorating condition.

It has been discovered that subjects who fail to regress their tumors fully after two or more implants nonetheless have acquired a protective immune response. In promoting the ability of this response to protect the subject against metastasis or regrowth at the primary site, it is beneficial to remove the residual tumor. This is typically accomplished by surgical excision where possible, but may also be performed by other methods in the art, including chemotherapy, radioablation, or immunotargeting. Accordingly, one embodiment of this invention comprises the additional feature of removing residual tumor at or around the site at a time subsequent to implanting of the second cell population, either before or after any additional implants are performed.

The pharmaceutical compositions of this invention may be given following or along with other therapies relating to treating cancer or generating an anti-tumor response in the subject. For example, the subject may previously or concurrently be treated by chemotherapy, radiation therapy, and other forms of immunotherapy and adoptive transfer. Where such modalities are used, they are preferably employed in a way or at a time that does not interfere with the immunogenicity of the compositions of this invention. The subject may also have been administered an immunogenic composition in order to stimulate an immune response. Suitable compositions may include tumor antigen vaccines, nucleic acid vaccines encoding tumor antigens, anti-idiotype vaccines, and other types of cellular vaccines, including cytokine-expressing tumor cell lines such as described in International Patent Application WO 98/04282.

This invention further contemplates combination therapies. In one example, the subject is given a cellular vaccine in addition to the multiple implants, most typically between or following the implants to provide an additional boosting of the immune system. Preferred cellular vaccines comprise a combination of stimulated allogeneic lymphocytes and autologous tumor cells. The preparation and use of vaccines of this nature is described in detail in International Patent Application WO 98/16238, which is hereby incorporated herein by reference in its entirety. These embodiments involve implanting alloactivated cells into tumor sites in the patient on at least two successive occasions, interspersed or followed by boosting the therapeutic effect or immunological response by administering to the patient a composition comprising alloactivated human lymphocytes allogeneic to the patient and an inactivated cell population consisting of tumor cells from the patient or their progeny.

Even in experiments with inbred rat strains and defined tumor lines, the response to implant therapy is heterogeneous. Thus, refinements to the timing of administration of compositions according to this invention is within the judgment of the managing clinician, and depends on the condition of the subject, the objectives of treatment, and concurrent therapies also being administered. During the course of therapy, the subject is also evaluated on a regular basis for general side effects such as a febrile response or excessive inflammation. Side effects are managed with appropriate supportive clinical care.

Pharmaceutical compositions: Alloactivated cells use according to this invention are prepared according to generally accepted procedures of pharmaceutical practice, as is appropriate for live cell populations.

Cell compositions intended for human use are generally prepared under sterile conditions, and then tested to ensure that they are sufficiently sterile and free of mycobacteria, culture additives, and other components of processing that might be deleterious to the patent. The preferred medium for resuspending the cells is isotonic saline, although other physiologically compatible buffers may be used, or the cells may be washed into a physiological buffer just before administration. The inclusion of carriers is permitted, such as a gel or clotted plasma to facilitate implantation into a void produced by removal of a solid tumor.

Cell compositions are often prepared from responder and stimulator cells in a service laboratory, and then shipped back to the clinical center for administration. The composition will often be packaged with a label or other written information indicating that it is for use in an implantation procedure or for administration to a particular patient. The method of use may also be described in the written information, but this is optional since the intended use will usually be known by the recipient clinician. Intention for use of the composition according to the sequential implant strategy can also be inferred from other information, such as the requisitioning and supply of the composition in the context of the patient's clinical history.

The examples presented below are provided as a further guide to the skilled practitioner, and are not meant to be limiting in any way.

EXAMPLES

Example 1

Mixed Lymphocyte Culture Procedure

Collection of responder PBMC from unrelated donor: Peripheral blood mononuclear cells (PBMCs) were collected by leukapheresis from normal healthy donors unrelated to the patient to be treated. Donors were pre-screened to test for complete blood count (CB C) with differential, Hepatitis A, B, and C, VDRL, and HIV-I.

Approximately 150 to 300 ml of leukapheresis suspension containing PBMC was collected from each donor, using standard blood donation procedures for supportive apheresis according to the manufacturers' instructions. The leukapheresis was performed using a Fenwall CS 3000 (Deerfield, EL) blood cell separator. A flow rate of 40 to 50 ml/min for 2 to 4 hours with lymphocyte yield of $2-4\times10^9$ processed a total donor blood volume of 7,000 to 12,000 ml to yield 200 to 250 ml of leukapheresis suspension having less than 1 ml of red cells. If a Cobe 2997 blood cell separator was used, the centrifuge rate was 5×g, the flow rate was up to 45 ml/min, and the collection rate was no more than or equal to 2.5 ml/min.

However, if donor pre-absolute lymphocyte counts were in the $0.6\times10^9$ to $1.0\times10^9$ range, as little as 150 ml of leukapheresis product was drawn. Hematocrit for the final product was 3.5%. At least one total blood volume was processed for 80% efficiency of lymphocyte collection.

The anticoagulant used was either 2% citrate or a citrate/anticoagulant ratio of ACDA-15 ml/citrate-100 ml; ACDB-25 ml/citrate-100 ml; or CPD-14 ml/citrate-100 ml. To obtain the utmost product purity, the actual and final product from the cell separator was transported as a pure concentrate of cells in autologous plasma. The cells were not washed, and no albumin was added.

Preparation of donor cells: The leukapheresis product was transported to the MC Oncology Research Laboratory for the production of allogeneic mixed lymphocyte cells (MLCs) for immunotherapy.

Cells were drained from the leukapheresis pack into two or three 250 ml centrifuge tubes, removing and setting aside 3 ml for sterility tests to be done during centrifugation. Cell concentrate was diluted with phosphate buffered saline (PBS) and centrifuged for 7 minutes at 2,000 rpm. Centrifugation was repeated twice for a total of three times to wash the cells free of the clotting factor in the donor's serum.

Three 1 ml aliquots from the 3 ml removed from the leukocyte suspension were placed into sterile capped tubes for sterility testing. The first 1 ml aliquot was added to thioglycollate medium (Difco, Detroit, Mich.) (30–35° C., 48 hr.); a second 1 ml was added to tryptic soy broth (Difco, Detroit, Mich.) (25–30° C., 48 hr.); and the third 1 ml was added to RPMI 1640 (GIBCO, Gaithersburg, Md.) with 10% heat inactivated FBS(RPMI-10%) and 1% L-glutamine, but without antibiotics.

Cells were spin washed twice at 150 g for 10 minutes in PBS to remove platelets. The supernatant was very carefully discarded as cells were in a slurry and not a pellet. Cells were resuspended in AIM V (GIBCO, Gaithersburg, Md.) supplemented with 2% heat inactivated FBS (2% AIM V) to 420 ml, and placed into a T-175 $CM^2$ flask.

Patient or donor blood was diluted 1:1 with sterile saline. For cell separation, 35 ml of cell suspension was carefully layered onto 15 ml Histopaque® 1.077 suspension medium (Sigma, St. Louis, Mo.) in each 50 ml tube and centrifuged at 250 g for 45 minutes. Centrifugation was started slowly and gradually increased to full speed. After centrifugation, the interface containing mononuclear cells between the Histopaque® suspension medium and the plasma layer was carefully collected with a 25 ml sterile pipet deposited into clean 50 ml centrifuge tubes, diluted with 2% AIM V Media 1:1, and centrifuged at 550 g for 7 to 10 minutes to form a cell pellet. Cells remained a minimum of time in the Histopaque® suspension medium, because it is toxic to the cells.

The supernatant was discarded, the pellet was resuspended in 2% AIM V and divided into two 50 ml centrifuge tubes to a total volume 40 ml, and centrifuged at 550 g for 5 minutes. After washing, the supernatant was discarded. The washing step was repeated twice for a total of three times. After the last wash, cells in each tube were resuspended in 50 ml of 2% AIM V. Aliquots of 1 ml of the resuspended cells were diluted to a ratio of 1:10 in 2% AIM V per tube, then further diluted 1:1 in Trypan Blue (Sigma, St. Louis, Mo.) to distinguish dead from live cells, and the live cells were counted in a hemocytometer. Cells were set at $2\times10^6$/ml with 2% AIM V.

Collection of stimulator PBMC from tumor patients: From 200 to 400 ml of peripheral blood cells were drawn from glioblastoma patients by vena puncture and placed into 250 ml centrifuge tubes, removing and setting aside 3 ml for sterility tests to be done during spinning. Blood cells in the centrifuge tubes were diluted with saline and centrifuged for 7 minutes at 550 g. Centrifugation was repeated twice for a total of three times to wash the cells free of the clotting factor in the patient's serum. Sterility testing was conducted as described above.

Cells were washed twice by centrifugation at 150 g for 10 minutes in saline to remove platelets, the supernatant was very carefully discarded, and 420 ml of cells were resuspended in a T-175 $CM^2$ flask in saline.

15 ml of Histopaque® 1.077 cell separation medium was added to twelve 50 ml centrifuge tubes, and 35 ml of cells suspended in saline were layered onto the Histopaque® 1.077 in each 50 ml tube. The cell suspensions were spun at 250 g for 45 minutes, starting centrifugation slowly and gradually increasing speed.

After centrifugation, the mononuclear cells at the interface between the Histopaque® cell separation medium and the plasma layer were carefully collected with a 25 sterile pipet into 2 sterile 250 ml centrifuge tubes and diluted with 2% AIM V to a final volume of 250 ml. The diluted mononuclear cells were centrifuged at 550 g for 7 to 10 minutes. For washing, the supernatant was discarded, then the cell pellet was re-suspended with 2% AIM V and centrifuged at 550 g for 5 minutes. The washing step was repeated for a total of three times.

After the last washing step, cells were re-suspended in 50 ml of 2% AIM V, 1 ml of the cell suspension was diluted 1:10 in 2% AIM V per tube, and the number of viable cells was determined by enumeration in a 1:1 in Trypan Blue as described above.

It is readily appreciated that this procedure is equally suitable for obtaining stimulator cells from healthy third-party donors.

Alloactivation: The isolated patient PBMCs were re-suspended at $10^7$ cells/ml in AIM V, 50 µg Mitomycin C (Bristol-Mayer Squibb, Princeton, N.J.) were added per ml of patient cell suspension, and the suspension of PBMCs was incubated at 37° C. for one hour to block response of the stimulator cells to the responder cells. After one hour of incubation, the excess mitomycin C was washed from the cells by alternate centrifugation (250 g for 5 min), and the cells were resuspended in AIM-V. After mitomycin treatment of the patient's PBMCs, the cells were added at a 20:1 to 10:1 donor cell:patient cell ratio to the donor culture).

For co-culture, the donor and mitomycin C-treated patient PBMC suspension was placed in a sealed sterile Fenwal tissue culture system especially designed for culture of PBMC for reimplantation into patients. Cells were passed in sealed systems via Fenwal cell transfer units and pumps according to the manufacturers instructions, and cultured in a 37° C. incubator for 48 hours.

Sterility testing of alloactivated cells: Two days prior to implantation of the cell suspension, the following three sterility tests were performed. 10 ml sterile aliquots were removed from each tissue culture bag, placed into sterile capped 15 ml centrifuge tubes, and centrifuged for 10 minutes at 450 g. In each tube, the pellet was resuspended in 3.0 ml of PBS. A 1 ml aliquot of the cell suspension was added to each of three sterile capped tubes containing 2 ml of thioglycollate broth, tryptic soy broth, or RPMI-10% and incubated for 48 hours. Each cell suspension was examined microscopically prior to implant to detect signs of microbial growth.

On the day of surgery, the cells were centrifuged out of their medium, washed two times with saline and re-suspended in platelet free, decalcified plasma obtained from the patient the previous day. The cells were transported to the operating room in plasma, then the plasma was re-calcified by the addition of calcium gluconate so that it clots just before implantation into the tumor bed.

The day of surgery a drop of collected cell pellet was again examined for sterility under the microscope. Just prior to clotting, a 100 µl aliquot of the cell suspension was added to 2 ml each of RPMI-10% without antibiotics, thioglycollate and tryptic soy broth in a sterile capped tube. The samples were then incubated for four days after surgery, and a running log was kept of this last sterility test.

Example 2

Clinical Trial Using Alloactivated Cells Implanted at the Tumor Sites

This experiment confirms that allogeneic cells alloactivated using patient leukocytes are effective in cancer treatment.

A Phase I/II clinical trial was conducted to examine the feasibility, tolerability, toxicities and clinical effects associated with a single intratumoral injection of allogeneic lymphocytes sensitized against patient alloantigens. This trial is conducted under the auspices of the appropriate ethical approval committee, and in accordance with a protocol under the U.S. Food & Drug Administration.

Eligible patients were men and women between 18 and 85 years of age. A total of ten patients were studied. Eight patients were enrolled in the trial, and two additional patients were treated off-study on a compassionate basis. Nine of ten patients had locally advanced, surgically unresectable pancreatic tumors; 40% of the patients had Stage II disease, 30% had Stage III disease and 20% had Stage IV disease. One patient with Stage I disease was 89 years old, declined surgery and was treated on a compassionate basis. Seven of ten patients had received no prior therapy, one patient had received prior radiation therapy and two patients had received prior radiation and chemotherapy.

Preparation of cells: The procedure for preparing the cytoimplant cells was generally in accordance with the main features of Example 1. Typically, a volunteer third-party donor for responder cells is screened by normal blood bank criteria for suitability. No special matching or identification of HLA type is performed. Whole blood or leukapheresis is collected from the patient to be treated; and leukapheresis is collected from the donor on the same day. Mononuclear cells are prepared from both patient and donor by centrifugation on Ficoll™, and counted to ensure that enough cells are present to prepare the intended dose. Patient cells are inactivated by treating for 1 hour with mitomycin C, and then washed.

The cells are combined at a donor:patient ratio of 10:1 to 20:1, depending on the number of patient cells available. The cells are suspended at $3 \times 10^6$ per mL in AIM 5 medium containing 2% fetal calf serum and antibiotics in a gas-permeable plastic bag, and incubated at 37° C. in an atmosphere of 5% $CO_2$/95% $O_2$. No cytokines or other growth factors are added. After three days, the cells are collected by centrifugation and washed. The cells are then transferred to the clinic in a medium suitable for administration. For the treatment of pancreatic cancer, the cells were suspended in a volume of about 10 mL isotonic saline.

Features of the cells are shown on the following table:

TABLE 1

Alloactivated Cells Administered to Humans with Pancreatic Cancer

| Patient | MLC Cell Ratio | Total Cell Dosage | Final Viability | Final Sterility | MLC CD3/** CD69 | MLC IL-2 (ng/mL)+ | MLC IFN-γ (ng/mL)+ |
|---|---|---|---|---|---|---|---|
| 001, LM | 10:1 | $1.76 \times 10^9$ | 91% | Sterile | NA | 2779 | 202 |
| 002, SA | 10:1 | $3.5 \times 10^9$ | 98% | Sterile | 11.8% | 10852 | 438 |
| 003, RW | 10:1 | $2.8 \times 10^9$ | 88% | Sterile | NA | 2334 | 383 |
| 004, OY | 20:1 | $5.9 \times 10^9$ | 92% | Sterile | NA | 1927 | 0 |
| 005, MR | 10:1 | $6.0 \times 10^9$ | 95% | Sterile | NA | 3941 | 298 |
| 006, OB | 20:1 | $6.04 \times 10^9$ | 96% | Sterile | NA | 118 | 0 |
| 007, BS | 10:1 | $5.8 \times 10^9$ | 93% | Sterile | NA | 7307 | 981 |
| 008, LM | 10:1 | $8.9 \times 10^9$ | 91% | Sterile | 18.6% | 1137 | 308 |
| 009, GS | 13:1 | $10.5 \times 10^9$ | 95% | Sterile | NA | 433 | 0 |
| 010, JH | 15:1 | $9.6 \times 10^9$ | 90% | Sterile | NA | 11858 | 291 |

Administration: The treatment was conducted as follows: A sufficient amount of whole blood or leukapheresis was collected from each patient to prepare the cultured cells used in treatment. The sample was forwarded to the Immunotherapy Lab, and used to prepare stimulator cells for allogeneic stimulation of third-party lymphocytes.

Three days later the cytoimplant cells were administered to the subject on an out-patient basis. Under light anesthesia, an injection needle was positioned into the tumor using an endoscopic ultrasound guided technique. The implant cells were rescued from culture, washed, suspended in about 10 mL of injectable isotonic saline, and delivered to the diagnostic service center. The cells were injected into the tumor mass, the device was removed, and the patient was allowed to recover.

Three patients were administered with a single dose of $3 \times 10^9$ implant cells. Four patients were administered with a single dose of $6 \times 10^9$ implant cells. Three patients were administered with a single dose of $9 \times 10^9$ implant cells.

Follow-up was done one day, one week, one month, and every three months after implantation. Criteria assessed included evidence of toxicity, survival, tumor response (endoscopic ultrasound and/or CT-scan), tumor markers (CEA/CA19-9) and Karnofsky performance score.

Results: Patients treated with $3 \times 10^9$ cells: Patient 001 was a 78 year old male with an unresectable clinical Stage IV tumor. The patient received treatment on a compassionate basis, and survived 6.5 months. Patient 002 was a 53 year old female with an unresectable Stage III tumor. The patient later presented with elevated total bilirubin and died at 4.2 months after developing liver metastasis. Patient 003 was a 60 year old male with unresectable Stage III tumor. There was a hospital admission for synocopal episode. The patient survived 20.8 months.

Patients treated with $6 \times 10^9$ cells: Patient 004 was a 52 year old male with an unresectable Stage II tumor. The patient was later admitted to hospital with biliary obstruction, cholangitis, and dehydration. This patient died 20.7 months after treatment. Patient 005 was an 89 year old female with a Stage I tumor, who was not a candidate for resection due to her age. She received treatment on a compassionate basis, and died 11.3 months later due to myocardial infarction. Patient 006 is a 54 year old female with an unresectable Stage III tumor. She was later admitted to hospital for intractable nausea, vomiting and dehydration, and subsequently for gastrointestinal hemorrhage. There was increased tumor size and liver metastasis. The patient died 4.3 months after treatment. Patient 007 is a 61 year old female with an unresectable Stage II tumor. On follow-up, there was elevated total bilirubin, and the patient was admitted with intractable nausea and vomiting, diarrhea, and dehydration, possibly related to colitis flare-up. The patient is still alive >13 months after treatment.

Patients treated with $9 \times 10^9$ cells: Patient 008 is a 55 year old female with an unresectable Stage 1V tumor. No serious adverse events were observed, and the patient is still alive >13 months after treatment. Patient 009 is a 54 year old male with an unresectable Stage II tumor. The patient was later admitted for two days for pain and nausea and vomiting. The patient died 11.7 months after treatment. Patient 010 is a 68 year old male with an unresectable Stage II tumor. No serious adverse events were observed, and the patient died 8.5 months after treatment.

Clinical Interpretation: Elevated bilirubin, liver enzymes and nausea/vomiting with dehydration were the most common serious adverse events documented which were considered to be due to obstruction of biliary stents. These adverse events were considered to be associated with the disease rather than the therapy. Because of its relationship to the timing of the administration of the cytoimplant, one adverse event (elevated total bilirubin, Grade 4) was considered possibly related to therapy. No other serious adverse effects were observed that were considered to be associated with therapy.

The median survival for all patients treated in this study was 11.5 months (range 4.2 to >21) with a mean survival of greater than 10 months. The 6 month, 9 month, and 12 month probability of survival was 80% (n=8), 60% (n=6), and 50% (n=5), respectively. The probability of greater than eight month survival by dose was 33% for $3 \times 10^9$ cells, 75% for $6 \times 10^9$ cells, and 100% for $9 \times 10^9$ cells. Comparison of median survivals of patients treated with cytoimplant to those treated with 5-fluorouracyl (median=4.2 months) or GEMZAR™ (median=5.7 months) was significant at $p<0.006$ and $p<0.004$, respectively.

Histomorphology: Histology slides were prepared from tissue samples from an 89 year old female diagnosed with pancreatic adenocarcinoma. At the time of diagnosis, the tumor was advanced and surgically unresectable. The only treatment performed on this patient was the injection of the tumor with $6 \times 10^9$ cytoimplant cells. The patient died of a myocardial infarct 11.5 months later.

One photomicrograph showed fibrovascular tissue with scattered individualized tumor cells. There is a dense lymphocytic and plasma cell infiltrate. Another field showed lymphocytes rosetting the separated tumor cells. The tumor cells were dark and shrunken, which is evidence of apoptosis. Another field showed scattered islands of necrotic tumor cells. There was a very dense infiltrate of lymphocytes, and lymphocytes appear to be trafficking into the site from adjacent venules. In a high magnification view there was clear evidence of direct contact between lymphocytes and necrotic tumor cells.

The histomorphology analysis provide clear evidence of a local response by cells of the patient after implantation of the alloactivated cells. The data are consistent with the cell response in the patient having a direct role in the beneficial effects of the treatment, as shown by direct contact between lymphocytes and necrotic tumor cells. To the limited extent that infiltrating cells are present in untreated pancreatic cancer, this type of direct contact is not observed.

Example 3

Measurement of the Degree of Alloactivation

In order to ensure the production of high quality effective MLC cells, a method of measuring the potency of the alloactivated cells can be employed. Only cell cultures with activity over and above unstimulated control cells should be used clinically. It is beneficial to compare the activity to the unstimulated control, since baseline activity of mononuclear cells from different individuals varies widely.

Several methods are available for measuring lymphocyte activation. Compared with unstimulated mononuclear cells, alloactivated cells reduce more Formazan dye and have more esterase activity. Turnover of XTT (a Formazan dye) can be easily demonstrated in a 96-well plate by colorimetric spectrophotometry at 470 nm (reference 650 nm). Activated cells typically show higher absorbance than controls. Lymphocyte activation can also be demonstrated by flow cytometric determination of esterase activity using the esterase substrate, fluorescein diacetate (FDA). T cells with high esterase are not determined using FDA and a Phycoerythrin-labeled CD3 antibody. Esterase activity can be accurately measured in a plate assay by using higher concentrations of FDA and determination of esterase activity by spectrophotometry at 494 nm (reference 650 nm) in a 96-well plate format. Background esterase activity inherent to serum-containing media is inhibited by addition of a competitive esterase inhibitor (~10 mM), arginine methyl ester. For the most part, these measures show good correlation with each other and with blastogenesis.

I: MTT Formazan Reduction Assay

This assay is used to enumerate live cells by ability for culture sample to reduce MTT to blue-green Formazan dye, and is also helpful for the distinguishing activated from inactive cells. It can be used for practically any cell in practically any media. The useful cell range is between $10^5$ and $5\times10^6$ per mL.

Reagents:
 96 well plates, flat bottom (not ELI SA plates)
 5 mg/mL MTT (Sigma) in PBS (frozen)
 20% SDS in 45% DMF, 0.2 N HCl (pre-warmed to 37° C.)

Procedure:
 Place 100 μL of culture media with cells in 96 well plate in duplicate or triplicate. Use 100 μL of media alone for controls. Leave first column blank.
 Add 10 μL of MTT to each well. Tap plate to mix. Cover plate and incubate 37° C. for 4 hours.
 Add 50 μL of SDS solution, avoiding bubbles. Tap to mix. If bubbles are present, blow on surface. Count plate at 570 nm (reference 650 nm).

II: XTT Formazan Reduction Assay
 This assay is used to enumerate live cells by ability for culture to sample to reduce XTT to red-orange Formazan dye, and is also helpful for the distinguishing activated from inactive cells. It can be used for practically any cell in practically any media. The useful cell range is between $10^5$ and $5\times10^6$ per mL.

Reagents:
 96 well plates, flat bottom (not ELISA plates)
 1 mg/mL MTT (2,3-bis(2-methoxy-4-nitro-5-sulfo-phenyl-2H-tetrasolium-5-carboxanilinide salt, Sigma) in PBS (fresh)
 1.53 mg/mL PMS (phenylmethanesulfonyl fluoride, Sigma) in PBS (frozen, protected from light)

Procedure:
 Place 100 μL of culture media with cells in 96 well plate in duplicate or triplicate. Use 100 μL of media alone for controls. Leave first column blank.
 Pre-mix PMS with XTT immediately before use (5 μL per mL XTT). Add 50 μL of XTT to each well. Tap plate to mix.
 Cover plate and incubate 37° C. for 4 hours. Count plate at 470 nm (reference 650 nm).

III: Flow Cytometry for CD3/CD69 or CD3/FDA
 This is a measurement of T lymphocyte activation after mixed lymphocyte alloactivation. Activities such as CD69 expression or esterase activity correlate with cytokine secretion and can be used as surrogate measures of lymphocyte activity. Unstimulated lymphocytes do not express surface CD69 and have only low levels of non-specific esterases. Once activated by alloantigens or non-specific mitogens, the expression of CD69 appears within 48 hours (peak at 24). Esterase activity increases shortly after stimulation, and continues for several days. Not all allostimulated lymphocyte reactions proceed with the same kinetics, and it is preferable to measure activation on day 1, 2 and 3 of the culture.

Sample:
 Test samples of donor and patient cells are mixed in small cultures at $0.5\times10^6$ cells/mL in 2% FCS-RPMI. These cultures are maintained at 37° C. in 5% $CO_2$ incubator until testing.

Reagents:
 Monoclonal antibodies:
  CD3-PE (Coulter)
  CD69-FITC (Becton-Dickinson). Keep refrigerated when not in use and protect from light.
  Fluorescein Diacetate (Sigma): Stock solution is prepared at 10 mg/mL DMSO, protected from light, and stored in frozen lot tested aliquots. Make working solution weekly by diluting stock 1:1100 in DMSO, keep working solution refrigerated and protected from light.
 D-PBS, 0.5% paraformaldehyde-0.05% TRITON™ X-100 in PBS Procedure:
 Internal control unstimulated and activated mononuclear cells samples are produced on an as-needed basis. Large lot-tested batches will be frozen in 250 μl aliquots in 10% DMSO freezing media.
 Mononuclear cells from a normal donors can be used to produce activated control specimens. These cells are placed in 2% FCS-RPMI at $0.5\times10^6$ cells/mL up to 100 mL. Cells are cultured for 2 days at 37° C. in the presence or absence of 2 μg/mL PHA lectin, or admixed at a ratio of 10:1 with a second donor population. The cells are collected by centrifugation at 350×g for 5 minutes. The media is removed and replaced by 1/10th the volume of DMSO Freezing media, and frozen. When needed, control unstimulated and stimulated cells can be thawed quickly and resuspended at the original volume by adding 9 volumes of PBS.
 Control cells are analyzed according to the protocol below along with samples from the test culture. The duplicate use of control specimens is an addition quality assurance measure. The percentage of CD69 or esterase positive lymphocytes should be within a 5% variance.
 Dilute 5 μL of CD3-PE antibody (per sample) in 0.5 mL PBS (per sample). Add either 10 μL CD69 (per sample) or 1 μL of working solution of FDA (per sample).
 To 12×75 mm labeled polystyrene tubes, deliver 0.5 mL of diluted antibody. Add 100 μL of well mixed sample to each tube, including reference controls, unstimulated donor cells and the alloactivated cells. Gently vortex and incubate 30 minutes at room temperature. Add 0.5 mL of 0.5% paraformaldehyde-0.05% TRITON™ X-100 PBS and mix.
 Counting is performed on an appropriately equipped flow cytometer, such as the EPICS XL Coulter Flow Cytometer. Histogram 1 (forward scatter vs. CD3) of either protocol should have a generous gate around the CD3+ mononuclear cells. Region A should approximate % T-Lymphocytes and should be passed to Histogram 2. In Histogram 2, the use of side scatter versus CD3 permits discrimination of lymphocytes (low side scatter level) from unlysed RBCs, RBC ghosts, platelet aggregates, residual granulocytes and other debris. A gate is drawn around the lymphocytes (see Histogram 2 for example). This second gate is passed to Histogram 3, where the CD3+ CD69+cells or CD3+ FDA+ cells are displayed. Run the control values first to set gates (unstimulated controls). Place the quad stat cursor of Histogram 3 so that the CD69 or FDA high values (Quad 2) are 2%. Leave this gate set when analyzing stimulated samples.
 Count at least 5,000 gated cells for each sample to obtain a 97% confidence interval.
 Cell Proliferation ($H^3$-Thymidine incorporation into DNA): Responder spleen cells are suspended at 1 million cells/ml in RPMI-1640 containing 10% fetal bovine serum, antibiotics (streptomycin/penicillin) and $5\times10^{-5}$ M 2-Mercaptoethanol. One hundred ul of these cells are seeded in triplicate wells of a u-bottom microtiter plate (Costar). Stimulator spleen cells are then prepared identical to responder spleen cells but are irradiated with 3000 R ($Cs^{137}$ sousrce) prior to use. One hundred ul of the stimulator cells are added and the mixed lymphocyte culture is incubated at 37 C. for 7 days in a 95% air/5% $CO_2$ atmosphere. After 7 days 10 ul of H³-thymidine (0.5 mCi/ml, ICN Pharmaceuticals, Costa Mesa, Calif.) is added to each well for 6 hours. The microtiter plate is then harvested used a MASH harvestor and the amount of incorporated thymidine determined by counting the harvested wells in a liquid scintillation counter. The stimulation index (SI) is then determined by calculating the ratio of the CPM of H3-Thymidine incorporated into the MLC culture divided by the CPM of H3-thymidine incorporated into the control (unstimulated) culture.

Potency assay determination by incorpotion of Acridine Orange (AO): Spleen cells are cultured at 1 million/ml in the same media as the cell proliferation assay but in 5×75 mm polypropylene tubes. Each tube receives 1 ml of reaction mixture. After 3 to 7 days of incubation at 37 C., the tubes are mixed by vortexing, and 200 ul removed and placed in a fresh 5×75 mm polypropylene tube. 50 ul of acridine orange (50 mg/ml in PBS) is then added for 15 minutes at room temperature. The tubes are again mixed by vortexing and the cells analyzed for the incorporation of acridine orange by flow cytometry. Results are expressed as the ratio of flourescence intensity of samples of MLC activated cells versus samples of control (unactivated) cells.

Blast assay (day 7): Spleen cells are cultured in 5×75 mm polypropylene tubes identical to the AO test. After 7 days at 37 C., the cells are mixed by vortexing and a cytospin preparation is made (Shandon cytocentrifuge,). The slides are stained with Wright/Giemsa stain using an automated slide stainer and the blasts enumerated manually by counting at least 300 cells/slide. The percent blasts is calculated by dividing the number of blasts by the total number of nucleated cells.

IV: FDA Plate Assay

This assay is used to enumerate live cells by ability for culture sample to turnover the esterase substrate, fluorescein diacetate, and is also helpful for the distinguishing activated from inactivated cells. This assay can be used for practically any media. The useful cell range is between $10^5$ and $5\times10^6$ per mL.

Reagents:
  96 well plates, flat bottom (not ELI SA plates)
  10 mg/mL FDA (Sigma) in DMSO (stock, protect from light)
  10 mg/mL Arginine methyl ester (Sigma) in DMSO Procedure:
  Place 100 µL of culture media with cells in 96 well plate in duplicate or triplicate. Use 100 µL of media alone for controls.
  Make a fresh working solution of FDA by adding 10 µL per mL of PBS of stock FDA plus 50 µL AME stock per mL. Add 20 µL of FDA working solution to each well. Tap plate to mix.
  Cover plate and incubate 37° C. for 1 hour. Count plate at 494 nm (reference 650 nm).

V: Acid Production Assay

This assay is used to quantitate relative organic acid production in cultures. This correlates with the state of activation of cells. This assay requires the use of medium containing no more than 2% serum. Practical cell range is $1-5\times10^6$ cells/mL incubated from 24–48 hours.

Reagents:
  96 well plates, flat bottom (not ELI SA plates)
  Acid Analysis Reagent. This is made in bulk and stored at 4° C. Add 0.1 mg/mL Bromophenol Blue in distilled water. Add sufficient concentrated HCl until the appropriate titration point is met. Titration is performed until yellow-green color is obtained after adding 75 µL of reagent to 100 µL RPMI 2% FCS in a well of a 96 well plate.

Procedure:
  Place 100 µL of culture media with cells in 96 well plate in duplicate or triplicate. Use 100 µL of media alone for controls.
  Add 75 µL of Reagent to each well. Tap plate to mix. Count plate at 470 nm (reference 650 nm).

VI: Blastogenesis Quantitation

This assay is used to quantitate the absolute number of lymphoblasts produced in cultures after 7 days. This assay can be used for peripheral blood mononuclear cells in practically any media. The useful cell range is between $1\times10^5$ and $5\times10^6$ per mL.

Reagents:
  Wright's Stain or Diff-Quick Stain

Procedure:
  Place 1–2 drops of a 7 day culture in a Cytospin chamber and perform Cytospin. Stain dried glass slide with either Wright's Stain or Diff-Quick Stain. Count number of lymphoblasts and other cells under oil immersion 100× lens of microscope. Count over 300 total cells.

Example 4

Experiments with Cultured Human Cells

Criteria for Functionality of Alloactivated Cells

The degree of alloactivation (a potential reflection of potency in therapy) can be measured according to the functional assays detailed in Example 3. This example illustrates the degree of activation revealed by the assays.

Human peripheral blood monocytes were isolated from samples taken from a number of unrelated human volunteers, and set up in one-way mixed lymphocyte cultures at a 10:1 responder:stimulator ratio as described elsewhere in this disclosure. The assays were run after 2–3 days in culture.

The results are shown in FIG. 1. Each of the individuals is indicated by a unique letter, with the responder cells being indicated before the stimulator cells. Thus, the designation A×B means that cells from individual A were cultured with inactivated cells from individual B.

Compared with unstimulated mononuclear cells, alloactivated cells have more esterase activity and reduce more XTT (a Formazan dye). Esterase activity can also be measured by flow cytometry using the esterase substrate, fluorescein diacetate (FDA). T cells with high esterase activity can be identified by Phycoerythrin-labeled CD3 antibody in conjunction with FDA. These measures correlate well with blastogenesis (determined after culturing for one week), or the level of IL-2 or IFN-γ in the supernatant.

Impact of Using Multiple Allogeneic Stimulator Cells

Alloactivated human lymphocyte cultures were produced using cells from either one, two, three or four unrelated donors. $3\times10^6$ cells/mL were cultured in 2% FCS-RPMI at 37° C. for 2 days. Two-donor populations were produced by admixing responder cells with stimulator cells at a 10:1 ratio. Populations containing three or four donor cells were produced by mixing responder cells with two or three different stimulator cells at ratios of 9:1:1 or 8:1:1:1.

Figure 2A:
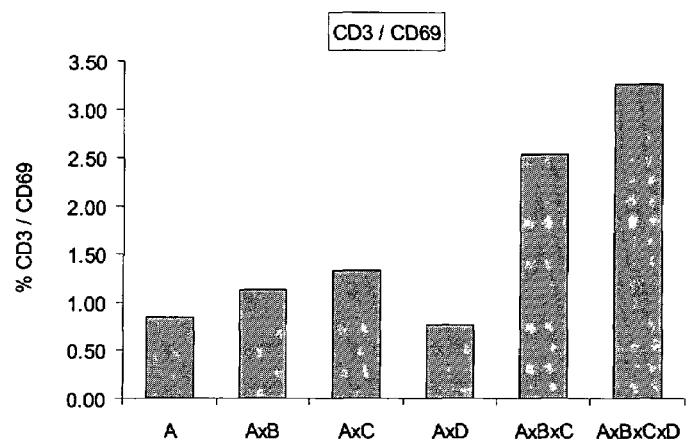
FIG. 2 is a bar graph showing the enhancement of alloactivation of human lymphocytes in culture by using a plurality of different stimulator cells.
Figure 2B:
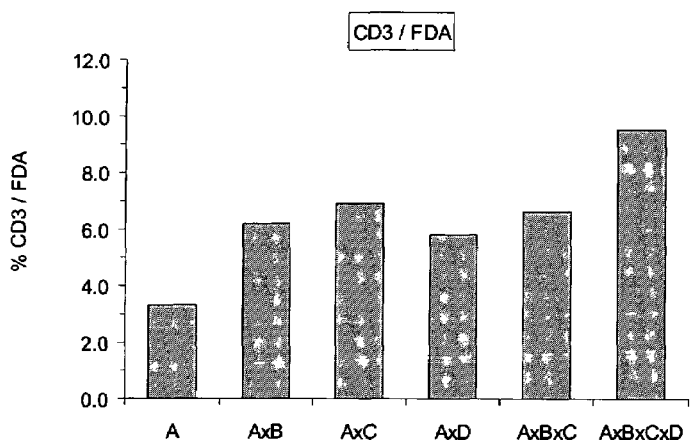

FIG. 2 shows the characteristics of the cells measured using flow cytometry. All values represent percentage of brightly fluorescent cells after counting 4000 cells on a Coulter EPICS XL Cytometer.

The results show that cultures prepared with stimulators from a plurality of donors in certain conditions reach higher levels of activation.

Impact of Altering the Ratio of Responder:Stimulator Cells

Mixed lymphocyte cultures composed of alloactivated human peripheral blood mononuclear cells were produced using cells from the same two unrelated donors at ratios of 20:1, 10:1, 5:1, or 1:1. Cells were cultured at $0.5 \times 10^6$ cells/mL in 2% FCS-RPMI for 3 days. The strength of these cultures was measured using the XTT Formazan reduction assay.

Impact of Histamine or Cimetidine on Alloactivation

Histamine is known to induce the activity of T suppressor cells. Since T suppressor cells can play a role in controlling the activity of the MLR, the effect of histamine and of a potent histamine type 2 (H2) receptor blocking drug, Cimetidine, was tested in allocating cell cultures. Cell populations composed of alloactivated human peripheral blood mononuclear cells were produced using cells from unrelated donors. All cultures contain a 10:1 ratio of responder: stimulator mononuclear cells at $0.5 \times 10^6$ cells/mL. In some cultures, 20 μg/mL histamine or 20 μg/mL Cimetidine were added on day 0.

According to the results measured using a Formazan reduction (XTT) assay, histamine induced suppression and decreased strength of the alloactivation. Cimetidine enhanced activity, possibly by blocking the development of suppression. The degree of enhancement in a 10:1 MLC was from 55 $OD_{470}$ units in the standard culture to 130 $OD_{470}$ units in the cimetidine supplemented culture.

Example 5

Commercial Production of Alloactivated Cell Compositions

This protocol describes the overall approach to production of the mixed lymphocyte culture. The design of this methodology takes into account Good Manufacturing (GMP) and Good Laboratory (GLP) Practices, and complies with requirements of Code 21 of U.S. Federal Regulations.

Patient peripheral blood mononuclear cells, at least $2 \times 10^9$ cells are collected by modified leukapheresis from the patient to be treated. Isolation of cells is performed on a Baxter Fenwall apheresis machine or equivalent machine using the Stem Cell Collection Procedure. Cells are shipped in a Baxter-type component bag on ice (4–10° C.). Transit temperature is monitored using MONITOR-MARK™ Time/Temperature Tags.

Donor peripheral blood mononuclear cells, at least $10 \times 10^9$ cells, are collected by modified leukapheresis from a healthy individual. Isolation of cells is performed on a Baxter Fenwall apheresis machine or equivalent, using the Stem Cell Collection Procedure. Donors are unrelated, anonymous, and random individuals, picked from a list of pre-screened potential donors.

Prescreening of the donors should indicate negative risk factors for HIV, Hepatitis, Spongioform Encephalitides, or Tuberculosis. Each cell component is tested negative for HIV 1/2 Ab, HIV Ag, CMV Ab, HTLV I/II Ab, HCV Ab, HBcAb, HBsAg and RPR. Cells are shipped in a Baxter-type component bag on ice (4–10° C.).

Upon receipt each component is tested for sterility, appropriate cell counts, and viability. Components are maintained at 4–10° C. until use, and used or frozen within 72 hours of collection. Thawed frozen material are used within 2 hours and not re-frozen. Pre-clinical studies indicate that components stored at 4° C. in ACD anticoagulated plasma or material frozen in DMSO-containing media are suitable for the production of effective cell compositions.

Plasma is removed form both the donor and patient components by centrifugation. Donor plasma may be collected and heat-inactivated for use as a medium supplement. Component cells are suspended in small volumes of PBS and appropriate volumes of each suspension is mixed to produce a culture that contains $3 \times 10^6$ mononuclear cells/ml in AIMV medium at a ratio of 10:1 to 20:1 (donor:patient cells). Heat-inactivated donor plasma is added to a final concentration of 2%. Mixed cells are pumped into Fenwall 3 liter gas permeable culture bags through the use of the Fenwall solution pump and sterile set-up. Samples of the component cells may also be set up in small culture tubes for testing of lymphocyte activation. Testing of functional activity is compared with control cultures containing unstimulated donor cells alone.

Cell mixtures are cultured in a ISO-°9000 Form a 37° C. incubator with 5% humidified and HEPA filtered $CO_2$ for 3 days, and closely monitored. Cells are harvested after culture by centrifugation. Samples are taken for quality assurance assays. Each preparation is tested for final sterility, adequate cell counts, adequate viability and functional activity.

The cell preparation is suspended in sterile 25% human albumin, and placed in sterile injectable vials for transport. Each preparation is labeled with an expiration date and time, which is 30 hours after packaging, and accompanied by appropriate instructions, release specification results, and a MONITOR-MARK™ Time/Temperature Tag. Cell preparations are packaged and shipped via overnight courier service. If not used immediately, the cells are stored in a refrigerator at 4–10° C. Any preparation not implanted before the expiration date is discarded.

In process tests that measure product consistency include:
pre-screen infectious disease tests;
in process and final product sterility tests;
final product mycoplasma and endotoxin;
in process and final product cell counts; in process and final product viability ($\geq 80\%$).

Cells must also meet satisfactory functional criteria. Preparations not meeting any of these criteria are not used for treating patients.

TABLE 2

Donor and Patient Screening
(At Time Of Leukapheresis Procedure)

| TEST | METHOD (AS PER HOSPITAL BLOOD BANK SOPS) | SPECIFICATION |
|---|---|---|
| Pre-screen for risk factors | HIV Hepatitis Spongioform encephalitis Tuberculosis | Report Only |
| Adventitious agent screening | HIV 1 and 2 Ab HIV Ag HBs-Ag HBc Ab* HCV Ab HTLV 1 and 2 Ab CMV Ab* RPR | All negative* |

*Patient may be positive for HBcAb or CMV Ab, and components are labeled as such.
If CMV negative donor components are not available, a CMV Ab positive donor component may be used, even for CMV negative patients.

TABLE 3

Pre-Process Testing Of Donor And Patient Mononuclear Cells
(At Time Of Receipt At Facility, Prior To Irradiation)

| TEST | SPECIFICATION |
|---|---|
| Sterility | Sterile |
| Cell Count | |
| Patient: | $\geq 2 \times 10^9$ cells |
| Donor: | $\geq 10 \times 10^9$ cells |

TABLE 4

In Process Testing Of Alloactivated Cells

| TEST | ASSAY | SPECIFICATION |
|---|---|---|
| Bioactivity of lymphocytes activation (Tests on days 1, 2, and/or 3 of culture) | Acridine Orange Assay (AO) | $\geq 10\%$ above unstimulated donor control value on any day of test |
| | Flow Cytometry (cell surface expression of CD69 by fluorescent antibody; or increased intracellular esterase activity by fluorescein diacetate) | $\geq 10\%$ above unstimulated donor control value on any day of test |

TABLE 5

Final Product Testing

| TEST | SPECIFICATION |
|---|---|
| Sterility | Sterile |
| Cell Count | $9 \times 10^9$ cells ($\pm 15\%$) |
| Viability | $\geq 80\%$ viable cells |
| Mycoplasma | Negative (results not available until after the implantation) |
| Endotoxin | $\leq 350$ EU/total body |

Example 6

Eradication of Established Tumors Using Multiple Intratumor Implants

This example describes animal experiments in which immunological treatment of established malignant tumors resulted in complete tumor regression and induction of permanent, long lasting tumor specific immunity.

The tumor selected for this study is a non-immunogenic glioma in the Fischer 344 (F344) rat, designated RT-2 (also known as D74). D74 is an extremely aggressive, transplantable tumor in the F344 rat with histologic and clinical characteristics of Glioblastoma Multiforme. It is essentially incurable by standard therapeutic protocols. Intracranial implantation of as few as 10 cells results in fatal brain tumors in about 40 days. When injected subcutaneously, as few as 500,000 cells form progressively growing tumors, first palpable in about 5 days, then progressing to large, 2 to 3 cm tumors in 3 to 4 weeks. D74 is not immunogenic on its own, as inoculation of naive rats with multiple doses of large numbers of lethally irradiated (10,000 rads) D74 tumor cells does not confer immunity. Surgical removal of well established growing tumors also does not result in subsequent immunity of the host.

Using the D74 tumor model, studies were conducted to determine the anti-tumor effects of intratumor implantation of allogeneic lymphoid cells. The allogeneic cells were sensitized against the alloantigens of the F344 rat (RT-1$^{lvl}$) by in vitro mixed lymphocyte culture (MLC).

Mixed lymphocyte cultures were established in the following manner. Spleen cells from F344 rats or allogeneic donor rats (Wistar or Sprague-Dawley) were aseptically removed and minced into single cell suspensions in phosphate-buffered saline (PBS). The cells were passed through fine mesh gauze to remove small particulate debris, and washed twice by centrifugation (1500 rpm). The F344 stimulator cells were then irradiated with 3000 Rads (Cs$^{137}$ source). Allogeneic responder cells were cultured at 3 million/mL in RPMI-1640 containing 10% fetal calf serum, antibiotics (streptomycin/penicillin) and $5\times10^{-5}$ M 2-mercaptoethanol; then stimulated with irradiated F344 spleen cells at a 10:1 responder:stimulator cell ratio. After 3 days at 37° C., the cells were harvested by centrifugation, washed twice in PBS, and suspended in PBS at 500 million/mL. This preparation is referred to in this example as a cytoimplant.

Cytoimplants were administered to F344 rats bearing established (4 to 7 mm) D74 tumors growing in the left thigh. The tumors were initiated approximately 10 days earlier by injecting naïve F344 rats subcutaneously with 0.5 million D74 cells suspended in 100 μL PBS. Cytoimplants were suspended in a tuberculin syringe fitted with a 25 gauge needle, and were injected directly into the tumor nodule in a volume of 100 to 250 μL.

Groups of F344 rats bearing well established D74 tumors (10 day tumors, 4 to 7 mm in diameter) received one of several treatment regimens: Group 1 received intratumor injections of 250 μL PBS alone on days 10 and 17 (control); Group 2 received a single intratumor injection of 150 million Wistar anti-F344 Cytoimplant cells in 250 μL PBS on day 10 only; Group 3 received an intratumor injection of 150 million Wistar anti-F344 Cytoimplant cells on day 10 followed by a second intratumor injection of Wistar anti-F344 Cytoimplant cells on day 17; group 4 received an intratumor injection of 150 million Wistar anti-F344 Cytoimplant cells on day 10 followed by a second injection of Sprague-Dawley anti-F344 Cytoimplant cells on day 17. Tumor sizes were measured bidirectionally using calipers 2 to 3 times/week, until the tumors reached 3.0 cm (at which time the animal became moribund and was sacrificed).

FIG. 3 shows the mean tumor size measured by calipers in each of the treated groups. Group 1: PBS control (●); Group 2: single implant of alloactivated cells at day 10 (■); Group 3: two implants of alloactivated cells from the same donor strain on days 10 and 17 (▲); Group 4: two implants of alloactivated cells from different donor strains on days 10 and 17 (♦). Day 0 is the time of injection of the D74 tumors; the arrows indicate the time of treatment with the alloactivated cells.

Figure 4:
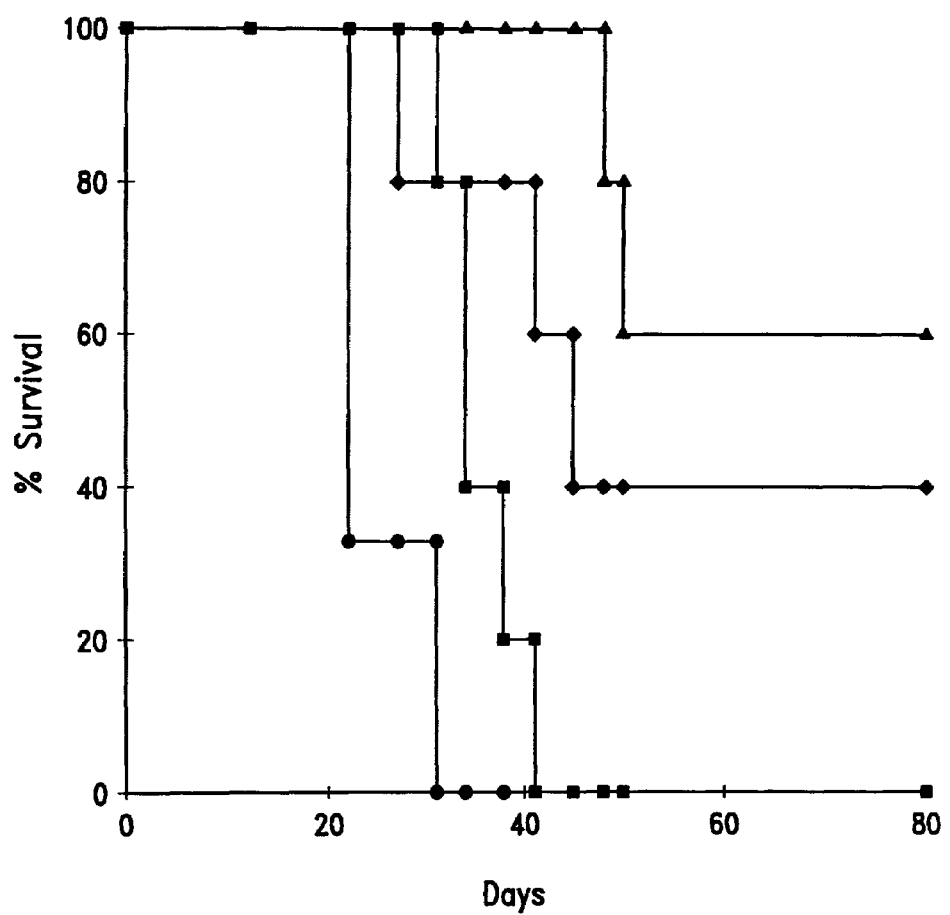
FIG. 4 is a Kaplan-Meier graph, showing the survival of rats in each of the treatment groups of FIG. 3. All animals in the control group (●) or the group receiving a single implant (■) eventually succumbed. However, 40 to 60% of animals in groups treated with two implants (▲, ♦) showed long-term survival.

FIG. 4 shows the Kaplan-Meier survival analysis of rats in each of the treatment groups.

These results demonstrate that subcutaneous D74 tumors grow rapidly in F344 rats and reached sizes of 3.0 cm in diameter in about 30 days (Control: Group 1). Intratumor implantation of 150 million Wistar anti-F344 Cytoimplant cells into 10 day well-established tumors (4 to 7 mm in size: Group 2) resulted in a significant slowing of tumor growth with an increase in median survival from 21 to 31 days. No animals in this group completely regressed their tumors and all ultimately died of progressive tumor growth. Intratumor injections of 150 million Wistar anti-F344 Cytoimplant cells at day 10 followed by a second similar injection at day 17 resulted in marked retardation of tumor growth (Group 3). Similar results were also noted when the second Cytoimplant (given at day 17) consisted of Sprague-Dawley anti-F344 cells rather than Wistar anti-F344 cells (Group 4), indicating that the result does not require identical donors in the two implants.

Figure 5:
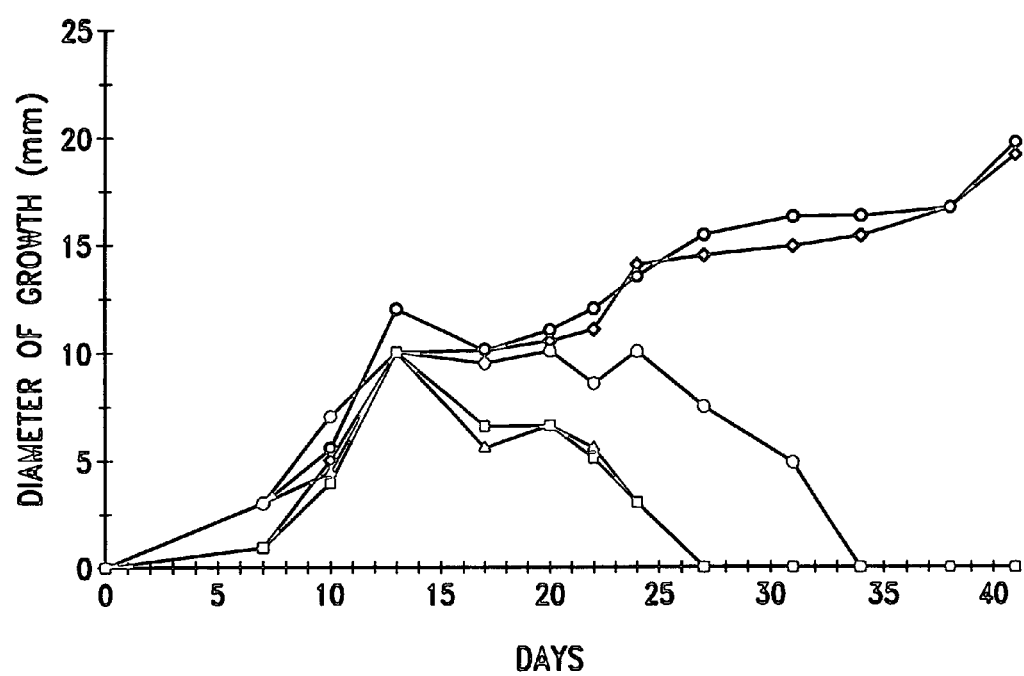
FIG. 5 is a line graph showing tumor growth for five individual rats in Group 3. Following treatment with two implants, 3 out of 5 animals (60%) showed essentially complete tumor regression. The animals showing complete regression were resistant to further challenge to D74 tumor cells given at another site, demonstrating that these animals had tumor-specific systemic immunity.

FIG. 5 shows tumor growth curves for individual rats in Group 3. Following treatment with two implants, 3 out of 5 animals (60%) showed essentially complete tumor regression (to less than 10% of maximal diameter). The other two animals did not eliminate the tumor. However, tumor progression was stabilized compared to animals in the control group (FIG. 1, Group 1) or with a single implant (FIG. 1, Group 2).

It should be emphasized that the anti-tumor effects of these double Cytoimplant treatments requires that the Cytoimplant cells are MLC-activated. In another series of experiments, established D74 tumors received double intratumor implantation with a similar number (150 million) of unactivated, allogeneic spleen cells or syngeneic spleen cells. The tumors in these animals grew at essentially identical rates to those in the control group.

Figure 6A:
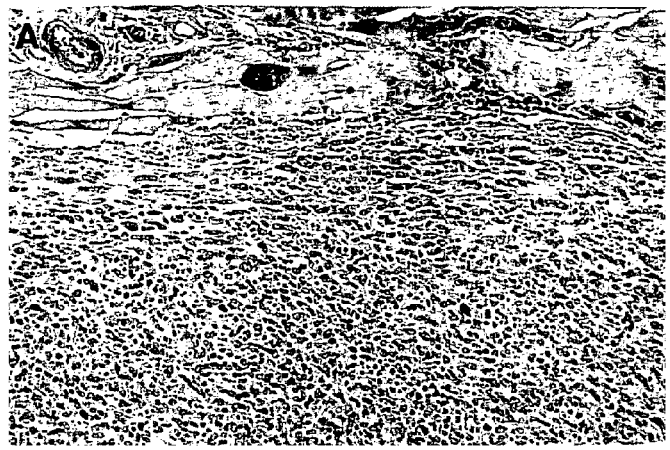
FIG. 6 is a photostatic reproduction of histopathology slides taken from treated animals. Top Panel: Control (Group 1), showing monotonous tumor cells and near complete absence of inflammatory cell infiltrates. Middle Panel: Animal treated with two implants (Group 3), showing marked inflammatory infiltrates and proliferation of fibroblasts and endothelial cells. Lower Panel: Higher power view of an animal from Group 3., showing a few remaining tumor cells undergoing apoptosis and necrosis.
Figure 6B:
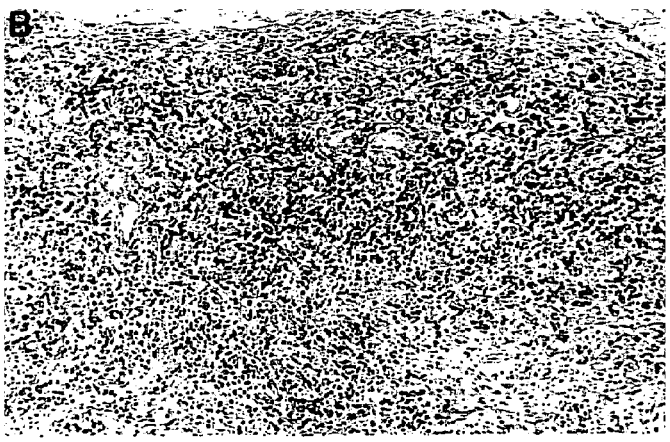
Figure 6C:
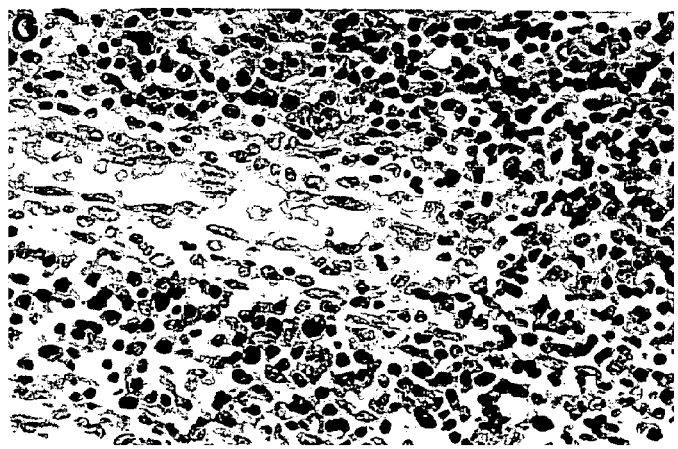

FIG. 6 shows the histopathologic analysis of tissue samples taken from animals in several of the treatment groups. This analysis was performed on hematoxylin/eosin stained sections taken approximately two weeks after the second Cytoimplant injection. Top Panel: Control, untreated D74 tumor (Group 1). Note the monotonous tumor cells with numerous mitotic figures and near complete absence of inflammatory cell infiltrates. Middle Panel: Tumor site 14 days after double implantation of Wistar anti-F344 spleen cells (Group 3). Note the marked inflammatory infiltrates, perivascular cuffing, and proliferation of stromal fibroblasts and endothelial cells. Lower Panel: Higher power view, showing deep penetrating vessel with marked perivascular cuffing of chronic inflammatory cells. There is infiltration of lymphocytes well within small tumor nests. The few remaining tumor cells are undergoing extensive apoptosis and necrosis.

The 40% of animals in Group 3 that did not show full tumor regression had at least managed to limit further tumor growth. These animals were rechallenged subcutaneously with lethal doses (1 million in 0.1 mL PBS) of D74 parental cells on the opposite flank. The results are shown in the following Table:

TABLE 6

Resistance to subsequent challenge in animals with regressed D74 tumors

| Treatment Group | No. of Animals | No. of Animals with Growing Tumors | |
|---|---|---|---|
| | | Rechallenge with D74 | Rechallenge with MADB106 |
| Wistar anti-F344 @ days 10 and 17 | 3 | 0/3 (0%) | 3/3 (100%) |
| Wistar anti-F344 @ day 10 followed by SD anti-F344 @ day 17 | 2 | 0/2 (0%) | 2/2 (100%) |
| Naive controls | 10 | 10/10 | N/A |

The data indicate that all animals who rejected their primary tumors also rejected the D74 parental challenge, indicating that systemic immunity to D74 had been established. The specificity of the immunity was also tested by rechallenging these same animals with a second unrelated but syngeneic tumor, MADB106 (breast adenocarcinoma). All animals which rejected the D74 challenge, progressively grew MADB106 tumors indicating that the immunity delaying the growth of the D74 cells was tumor specific.

Example 7

Longlasting Anti-Tumor immunity in Animals Treated with Multiple Implants Followed by Surgical Excision The studies described in the previous example revealed that replicate intratumor implants of Cytoimplant cells into established tumors can result in the induction of tumor specific immunity. For animals that did not show full tumor regression, the growth of the tumor was markedly retarded. It was concluded that the animals has been induced to respond against its tumor, but were not fully capable of causing its complete destruction. To test this possibility, animals which had received two intratumor Cytoimplants but which did not fully regress their tumors, had their tumors surgically removed. These animals were then tested for resistance to further tumor challenge.

Histologically, these tumors also showed considerable inflammatory changes similar to the changes seen in fully regressing tumors. Present throughout these tumors were mononuclear lymphoid infiltrates, perivascular cuffing and evidence of tumor cell necrosis and apoptosis. However, the intensity of this effect was less that that observed in tumors undergoing complete regression. In addition, there was a considerable amount of perivascular fibrosis which was not seen in tumors which completely regressed.

Ten days after the surgery, when the animals had fully recovered, they were challenged with lethal doses of D74 tumor cells in the opposite flank (1 million cells in 100 μL of PBS). The results for individual animals are shown in the following table.

TABLE 7

Long-lasting systemic anti-tumor immunity following double implantation and surgical excision

| Animal # | Primary Treatment (intratumor injections) | Tumor size at Surgery (mm) | Response to D74 Parental Challenge | Tumor Recurrence at Surgical site |
|---|---|---|---|---|
| AI037 #10 | Wistar anti-F344 at days 10 and 17 | 22 × 18 | Rejection | No |
| AI045 #11 | SD anti-F344 at days 12 and 19 | 27 × 19 | Growth | No |
| AI045 #12 | SD anti-F344 at days 12 and 19 | 21 × 18 | Rejection | No |
| AI045 #13 | SD anti-F344 at days 12 and 19 | 24 × 24 | Growth | Yes |
| AI045 #01 | PBS | 24 × 23 | Growth | Yes |
| AI049 #01 | PBS | 22 × 21 | Growth | Yes |
| AI049 #02 | PBS | 26 × 23 | Growth | Yes |

As the data indicate, surgical excision of D74 tumors which had previously received two intratumor cytoimplants (second cytoimplant was given 15 to 24 days prior to surgery) resulted in 2 of 4 rats (50%) rejecting a subsequent D74 parental challenge. In contrast, surgical excision of similarly sized D74 tumors which received intratumor injections of saline resulted in tumor growth in 3/3 rats (100%). Moreover, one of these control rats regrew D74 tumor at the surgical excision site, whereas animals which rejected the parental D74 challenge did not regrow tumors at the surgical excision site.

Example 8

Human Clinical Trials of the Multiple Sequential Implant Strategy

This example describes an open label randomized trial for comparing the safety and efficacy of systemic chemotherapy (Gemcitabine) to a Multiple cytoimplant strategy as first-line therapy for patients with unresectable locally advanced and metastatic pancreatic cancer.

Approximately 150 previously untreated patients in about 10 participating clinical centers are randomized for treatment with either cytoimplant or Gemcitabine. Enrollees are men or women 18 years of age or older, with histologically proven adenocarcinoma of the pancreas, Stages II, III, and IV, which is unresectable based on vascular invasion, lymph node metastasis or distant metastasis.

About 100 patients receive a course of immunotherapy consisting of two cytoimplants. Each cytoimplant consists of approximately nine billion cells injected directly into the primary pancreatic tumor via endoscopic ultrasound-guided fine needle injection. The first cytoimplant is administered on day zero and the second during month five. The other ~50 patients receive a continuous course of chemotherapy comprising Gemcitabine administered intravenously.

Patient Inclusion Criteria: Patients must be 18 years of age or older, male or female patients are eligible. Karnofsky performance score (KPS) must be 70 or greater. Patients must have histologically proven adenocarcinoma of the pancreas, bidimensionally measurable or evaluable (visible) by CT and must be unresectable based on vascular invasion, lymph node metastasis or distant metastasis. Patients with distant lymph node metastasis are considered unresectable. Patients with local or regional lymph node metastasis (N1) are also considered unresectable. Patients must be able to understand and sign the informed consent, and understand and complete the Subject Questionnaire. Female patients must not be lactating and must be either surgically sterile (via hysterectomy or bilateral tubal ligation), post menopausal or using acceptable methods of contraception if they are of child bearing potential. Female patients of child bearing potential must also have a negative serum pregnancy test. Expected survival must be greater than three months. Furthermore, eligible patients must meet the following laboratory parameters: WBC>3,500/μL; Platelets>100,000/μL; Hematocrit>33% or Hemoglobin>10.5 gm/dL; Total Bilirubin<3.0 mg/dL; SGOT (AST) or SGPT (ALT)<3×upper limits of normal value; Prothrombin time within 3 sec of control; Serum Creatinine<1.5 mg/dL; Serum Calcium<11.0 mg/dL. Patients must agree to receive all treatment and follow-up assessments at the investigational site. Patients must meet institutional requirements for apheresis procedures at the respective study site.

Patient Exclusion Criteria: History of previous myocardial infarction within three months preceding this study or clinical symptoms of congestive heart failure; concurrent medical condition requiring systemic steroid therapy; documented HIV infection; history of prior chemotherapy, radiation therapy or therapy with biologic response modifiers (interferons, interleukins); prior surgery within 30 days of execution of informed consent; persistent fever greater than 39° C. unless clinically assessed to be caused by tumor; primary malignancy (present or remote) of sites other than the pancreas, except for basal cell epithelioma of the skin; use of investigational drugs within 30 days of execution of informed consent; or clinically significant third space (symptomatic) fluid collection (e.g. ascites, pleural effusion).

Gemcitabine Arm

Within ten days after randomization, patients allocated to the Gemcitabine treatment group begin a continuous course of intravenous chemotherapy using Gemcitabine administered on an out-patient basis. If day 10 falls on a weekend or holiday, therapy is optionally started on the next working day. On the day of the first Gemcitabine infusion but prior to administration, blood is drawn for Lab C tests.

Gemcitabine (GEMZAR™) is administered by intravenous infusion at a dose of 1000 mg/m$^2$ over 30 min once weekly for up to 7 weeks (or until toxicity necessitates reducing or holding a dose), followed by a week of rest from the treatment (first cycle).

Subsequent cycles consist of infusions once weekly for 3 consecutive weeks out of every 4 weeks. Dosage adjustment is based upon the degree of hematologic toxicity experienced by the patient. Clearance in women and the elderly is reduced and women are somewhat less able to progress to subsequent cycles.

Patients receiving Gemcitabine are monitored prior to each dose with a complete blood count (CBC), including differential and platelet count. If marrow suppression is detected, therapy should be modified or suspended. For neutrophil and platelet counts of >1000 and >100,000 respectively, 100% of the dose is given. For patients with counts of 500–999 or 50,000–99,000, respectively, 75% is given. For patients with counts of <50 or <50,000, respectively, treatment is suspended. Laboratory evaluation of renal and hepatic function, including transaminases and serum creatinine, is also performed prior to initiation of therapy and periodically thereafter.

Patients who complete an entire 7 week cycle of Gemcitabine therapy (first cycle) or a subsequent 3 week cycle at a dose of 10 mg/m$^2$ may have the dose for subsequent cycles increased by 25% (to 1250 mg/m$^2$) provided that the absolute granulocyte count (AGC) and platelet nadirs exceed 1500×10$^6$/L and 100,000×10$^6$/L respectively, and if nonhematologic toxicity has not been greater than WHO grade 1. If patients tolerate the subsequent course of Gemcitabine at a dose of 1250 mg/m$^2$, the dose for the next cycle can be increased to 1500 mg/m$^2$ provided again that the AGC and platelet nadirs exceed 1500×10$^6$/L and 100,000×10$^6$/L respectively and, again, if nonhematologic toxicity has not been greater than WHO grade 1.

Cytoimplant Arm

Within ten days after randomization, patients allocated to the cytoimplant arm begin a course of immunotherapy comprising two cytoimplants. The first cytoimplant is administered at time period zero and the second during month five. Each cytoimplant consists of approximately nine billion cells injected directly into the primary pancreatic tumor via endoscopic ultrasound-guided fine needle injection (EUS-FNI) On the day of each cytoimplant administration but prior to injection, blood is drawn for Lab C tests.

Cytoimplant cells are prepared as follows: A genetically unrelated, healthy adult giving informed consent is recruited as pheresis donor. Not more than two days prior to scheduled production of the cytoimplant, donor peripheral blood mononuclear cells (PBMC) are collected in a standard "Baxter" or "Baxter equivalent" bag during a single modified leukapheresis procedure (peripheral stem cell collection). Lab tests are conducted on blood samples collected during donor screening and at each donor pheresis collection procedure for blood matching and to eliminate donor material that potentially contains infectious agents. These tests include ABO and Rh blood group typing, and assays for HTLV-1/2 Ab, VDRL (or RPR), $HB_sAg$, $HB_cAg$, HCV-Ab, and CMV-Ab.

Not more than two days prior to scheduled production of the cytoimplant, approximately five billion patient PBMC (stimulator cells) are collected in a similar fashion as described for the donor. If the patient has poor venous access, a central venous access may be used. Both donor and patient cells are transported at 1 to 10° C. by overnight delivery to the cell production laboratory. Upon arrival at the cell production laboratory, the donor and patient PBMC are inspected for physical damage.

The patient and donor PBMC are used to prepare the patient's cytoimplant according to the methods described elsewhere in this disclosure, and tested for sufficient activation of the responder population. See Example 3. Each cytoimplant is suspended in approximately 10 cc of sterile injectable saline supplemented with donor serum, and placed in a sealed sterile 10 cc syringe. The cells are then shipped overnight to the clinic for administration the following morning.

Electronic Ultrasound (EUS) is a procedure in which an endoscope with an ultrasound transducer mounted on the tip is guided into the stomach and duodenum. Because of the ultrasound probe, the device can image through the wall of the GI tract, allowing for high resolution visualization of adjacent structures such as the pancreas, and is the optimal modality for the detection of pancreatic cancers less than 3 cm in size. EUS can be combined with a Fine Needle Aspiration (FNA) technique. See: Chang K J et al., Gastrointest. Endosc. (1994) 40:694; Wierseman M J et al., Gastrointest. Endosc. (1994) 40:700; Vilmann P et al., Gastrointest. Endosc. (1995) 41:230; and Chang K et al., Am. J. Gastronenterol. (1994) 89:263. Recently, the EUS-guided FNA technique has been modified as an injection modality to deliver therapies such as the CYTOIMPLANT directly into the tumor. Termed EUS-guided Fine Needle Injection (FNI). Chang K. et al., Gastroenterology 112: A346, 1996.

The cytoimplant is administered to each patient by EUS-guided needle injection using a Pentax® Model FG32UA, Pentax® Model EG363OU, or Olympus® Model GFUC30P echoendoscope. Color flow mapping/Doppler is applied both to the lesion and its surrounding structures to assess vascularity. A 22-gauge GIP/Medi-Globe Hancke/Vilmann, 19-gauge GIP/Medi-Globe, or 22-gauge Olympus® NA-10J-1 needle is then guided ultrasonically into the primary pancreatic tumor.

The endoscope needle is primed with sterile preservative-free saline (approximately 2 mL). Immediately prior to injection, the syringe containing the implant cells is removed from storage, and visually inspected for suitability and a minimum required cytoimplant dosage of ~9.5 cc. The syringe containing the cytoimplant is then locked onto the top of the endoscope needle. Injection of the entire contents of the syringe (approximately 9 billion cells) is performed slowly (over 1–2 minutes) under real time ultrasound guidance into the primary pancreatic tumor. The procedure is performed at the study center under conscious sedation. Following injection of the cytoimplant, 2 cc of injectable preservative-free saline is injected into the endoscope needle to clear all cells.

Cytoimplant patients return to the study center the day following each injection for follow-up assessment. For the seven day period immediately following injection of the cytoimplant, patients are provided with a supply of acetaminophen, to be taken as needed (not to exceed two 500 mg tablets every four hours) for low grade (<102° F.) fever.

Patients in this treatment arm receive a second cytoimplant during month five. The second cytoimplant is produced a manner essentially identical to that of the first, using a different donor who is genetically unrelated to either the patient or the donor for the first cytoimplant. Again, the dose is approximately nine billion cells. Immediately prior to administration of the second implant, the primary pancreatic tumor is aspirated using EUS-guided FNA consisting of at least five needle passes for further analysis. The second cytoimplant is then administered into the tumor bed in essentially the same manner as the first.

Assessment

Follow-up visits are conducted regularly to monitor for serious and secondary adverse effects, and the efficacy of treatment. Therapeutic protocol is modified and adverse effects are managed as required. Follow up visits include the following tests: Day 1: physical examination including assessment of signs and symptoms of pancreatic cancer, weight, adverse event assessment, concurrent medication review, and KPS assessment, and Lab A tests. Month 1: Questionnaire, Lab A, Lab C, and abdominal CT Scan. Month 3: Lab A, Lab C, abdominal CT Scan. Cytoimplant arm, Month 5: Lab C, and EUS-guided fine needle aspiration of primary tumor followed by administration of the second cytoimplant directly into primary pancreatic tumor by EUS-guided fine needle injection. Day after second implant: Follow-up visit, and Lab A. Each of Months 5, 7, 9, and 12: Lab A, Lab C, and abdominal CT Scan. Samples of patient blood collected at each follow-up visit is collected for later analysis.

Evaluation of Efficacy: The Primary Endpoint is Survival. A positive result is relative improvement in overall survival measured from the date of randomization to date of death.

One Secondary Endpoint is Objective Tumor Response, classified in one of the following four categories: Complete Response (CR): Disappearance of all measurable and evaluable disease for a minimum of four weeks as documented by CT scan. Partial Response (PR): A decrease from baseline in total tumor mass (the sum of the largest cross sectional area(s) of all measurable disease as determined by digital tracing methods) of at least 50% without increase in evaluable disease or the appearance of new lesions for a minimum of four weeks as documented by CT scan. Baseline is defined as the CT scan obtained during the patient enrollment screening. Stable Disease (SD): A decrease from baseline in total tumor mass of less than 50% or an increase in total tumor mass not more than 25% without the appearance of new lesions all as documented by CT scan. In the absence of CR, PR or Progressive disease twelve weeks after randomization, patients are considered as SD. Progressive Disease (PD): An increase from baseline in total tumor mass of more than 25%, or the appearance of new lesions, all as documented by CT scan, or clinical progression. Clinical progression is defined as a decrease in Karnofsky performance score of greater than or equal to 30 points over two consecutive measurements more than four weeks apart using the patient enrollment screening KPS score as the baseline; or documented objective evidence of deterioration in clinical status consistent with disease progression such as unexplained weight loss of more than 20% from enrollment weight, tumor related pain requiring neuromuscular block, development of CT documented ascites, or new findings on physical exam consistent with progression.

Assessment of changes in tumor size are conducted at a central site using digital tracing. The radiologist conducting the assessments is blinded to the study treatment. At the time of each scan, a computer diskette or second original of the CT image is generated and sent to the central review site. The central radiologist selects from each successive scan the spot film depicting the largest cross-sectional tumor area. Each selected spot film is converted into a digital image by a computer scanner and stored. The perimeter of the tumor on each digitized image is then traced and the cross-sectional area calculated using computer graphics software. Changes in cross-sectional area are calculated and used to evaluate response.

Another Secondary Endpoint is Progression Free Survival, defined as the interval in days measured from the date of randomization to the date the patient is classified as having progressive disease or death. Information on progression free survival is gathered only while the patient is on-study. Patients who cease scheduled follow-up assessments prior to disease progression are censored at the time of last follow-up assessment for purposes of this analysis.

Yet another Secondary Endpoint is Time to Treatment Failure, defined as the interval in days measured from the date of randomization to the first date of the first to occur of (a) progressive disease, (b) treatment related adverse events requiring discontinuation of therapy, (c) patient refusal to continue therapy, or (d) death. Patients who cease scheduled follow-up assessments when none of the foregoing events have occurred are censored at the time of last follow-up assessment for purposes of this analysis.

A further Secondary Endpoint is Quality of Life. Quality of life is evaluated based on Karnofsky performance status, and using patient responses to the Subject Questionnaire. The life questionnaires consist of a Follow-up Visit (FUV) Subject Questionnaire and a Baseline Subject Questionnaire. The FUV Subject Questionnaire is composed of the Short Form-36 Health Survey (SF-36), the Functional Assessment For Cancer Therapy-pancreatic cancer (FACT-pa) questionnaire, and an economic questionnaire. The Baseline Subject Questionnaire is composed of the same questionnaires but also includes patient demographic questions. The Baseline Subject Questionnaire is administered during the patient eligibility screening period. The FUV Subject Questionnaire is administered at each of the scheduled follow-up visits.

Toxicities are monitored according to the NCI common toxicity criteria. Possible toxicities of the cytoimplant include fever, chills, nausea, vomiting, jaundice and pancreatitis. Other possible toxicities include shortness of breath, arrhythmias and peripheral edema. Possible expected toxicities of Gemcitabine include nausea, vomiting, fever, rash, diarrhea, bone marrow suppression, hair loss, elevated liver function tests, proteinuria and hematuria. Liver tests, including transaminase, bilirubin, and alkaline phosphatase (ALP), are commonly elevated in patients with pancreatic cancer due to the obstruction of the common bile duct. Pancreatitis is also monitored by following serial amylase/lipase determination as well as clinical status.

The randomization of patients between cytoimplant and Gemcitabine treatment arms is at a ratio of 2:1. Patients are stratified by disease stage in two levels. Strata one consists of patients with locally advanced, unresectable (Stage II and III) and strata two consists of metastatic (Stage IV) pancreatic cancer. The primary efficacy analysis is conducted 9 months after the last patient is randomized. Assuming exponential survival distributions, statistical significance based on a two-tailed alpha level of 0.050, and enrollment occurring over a six month period, this sample size provides greater than 85% power to detect an increase in median survival of from 6 to 12 months. Preliminary determinations may be obtained at an earlier time or following recruitment of a smaller patient population.

Both primary and secondary efficacy endpoints are analyzed based on the intent-to-treat population defined as all patients who have been randomized to a treatment group. The primary analysis is based on a proportional hazards model, stratifying for stage (Stage II and III vs. Stage IV) and is conducted approximately nine months following the date the last patient is randomized. Supplementary analyses are done based on an efficacy evaluable population defined as all patients receiving at least one cytoimplant or completing at least four Gemcitabine infusions or the first Gemcitabine cycle (whichever occurs first), and who are evaluated at the one month follow-up visit.

Although the invention has been described and illustrated in this disclosure to facilitate understanding, the skilled artisan will readily appreciate that modifications can be introduced during practice without departing from the invention. Accordingly, the description and illustrations should not be construed as limiting the scope of the invention, which is delineated by the following claims.

What is claimed as the invention is:

1. An improvement in the method of treating a human patient having a tumor by implanting at or around the site of a solid tumor in the patient a cell population comprising alloactivated lymphocytes that are allogeneic to the patient;
   wherein the implanting of the alloactivated lymphocytes in the patient generating a therapeutic response against tumor growth;
   the improvement comprising implanting at or around the site of a solid tumor in the patient a second cell population containing alloactivated lymphocytes that are allogeneic to the patient between 1 and 8 weeks after the implanting of the first cell population.

2. The improved method of claim 1, which elicits an inflammatory response against the tumor.

3. The improved method of claim 1, which elicits the immune response against the tumor.

4. The improved method of claim 1, wherein the alloactivated lymphocytes in at least one of the cell populations are alloactivated against leukocytes of the human patient.

5. The improved method of claim 1, wherein the alloactivated lymphocytes in at least one of the cell populations are alloactivated against leukocytes of a third-party donor different from the patient or the donor of the lymphocytes.

6. The improved method of claim 1, wherein treatment according to the method has at least one of the following effects in at least 30% of treated subjects:
   a) substanial regression of the tumor in size;
   b) lack of recurrence of a tumor after removal; or
   c) decrease in rate of formation of metastasis.

7. The improved method of claim 1, wherein the tumor is a cancer is selected from melanoma, pancreatic cancer, liver cancer, colon cancer, prostate cancer, and breast cancer.

8. The improved method of claim 1, wherein the first cell population stimulates a response in the patient against the tumor before the implanting of the second cell population.

9. The improved method of claim 1, wherein treatment according to the method causes lack of recurrence of a tumor after removal.

10. The method of claim 1, wherein the first and second cell populations are implanted at or around the site of the same tumor in the patient.

11. The method of claim 1, further comprising removing any residual tumor at or around the site of the second cell population at a time subsequent to when the second cell population was implanted.

12. The method of claim 1, wherein both the first and second cell populations have one or more of the following features:
   i) contain between about $2\times10^9$ and $2\times10^{10}$ cultured peripheral blood mononuclear cells originating from the donor and between about $1\times10^8$ and $2\times10^9$ cultured peripheral blood mononuclear cells originating from the patient or from a second donor;
   ii) are obtained by a process in which donor lymphocytes are allocated by coculturing ex vivo with stimulator leukocytes for a period of about 48 to 72 hours; or
   iii) are obtained by a process in which donor lymphocytes are alloactivated by coculturing ex vivo with stimulator leukocytes and harvested at about the time of initial alloactivation, measurable by acridine orange or CD89 assay.

13. A product in which the following components are packaged together:
   a pharmaceutical composition comprising alloactivated lymphocytes allogeneic to leukocytes in a cancer patient; and
   written information for the treatment of the patient according to the method of claim 1.

* * * * *